US008088597B2

(12) United States Patent
De Roos et al.

(10) Patent No.: US 8,088,597 B2
(45) Date of Patent: Jan. 3, 2012

(54) BLOOD PRESSURE LOWERING PEPTIDES FROM GLYCOMACROPEPTIDE

(75) Inventors: Andre Leonardus De Roos, Delft (NL); Pieter Marinus Van Den Broecke, Didam (NL); Luppo Edens, Rotterdam (NL)

(73) Assignee: DSM IP Assets B.V., Heerlen (NL)

( * ) Notice: Subject to any disclaimer, the term of this patent is extended or adjusted under 35 U.S.C. 154(b) by 514 days.

(21) Appl. No.: 11/884,448

(22) PCT Filed: Feb. 23, 2006

(86) PCT No.: PCT/EP2006/060198
§ 371 (c)(1),
(2), (4) Date: Mar. 19, 2008

(87) PCT Pub. No.: WO2006/089921
PCT Pub. Date: Aug. 31, 2006

(65) Prior Publication Data
US 2008/0161227 A1 Jul. 3, 2008

(30) Foreign Application Priority Data

Feb. 24, 2005 (EP) .................................. 05101417
Nov. 1, 2005 (EP) .................................. 05110236

(51) Int. Cl.
*C12P 21/06* (2006.01)
*A61K 38/06* (2006.01)
(52) U.S. Cl. ....... 435/68.1; 530/331; 530/360; 514/21.9
(58) Field of Classification Search ................. 435/68.1; 530/331
See application file for complete search history.

(56) References Cited

U.S. PATENT DOCUMENTS

| | | | | |
|---|---|---|---|---|
| 5,061,622 A | * | 10/1991 | Dosako et al. ............... | 435/68.1 |
| 5,075,424 A | * | 12/1991 | Tanimoto et al. ............ | 530/361 |
| 5,280,107 A | * | 1/1994 | Kawasaki et al. ............ | 530/361 |
| 5,391,497 A | * | 2/1995 | Menon et al. ............... | 435/320.1 |
| 5,968,586 A | | 10/1999 | Etzel ............................ | 426/657 |
| 6,168,823 B1 | * | 1/2001 | Etzel ............................ | 426/656 |
| 6,232,094 B1 | * | 5/2001 | Hansson et al. ............. | 435/69.1 |
| 6,323,008 B1 | * | 11/2001 | Pelletier et al. .............. | 435/84 |
| 6,555,659 B1 | * | 4/2003 | Ayers et al. ................. | 530/395 |

FOREIGN PATENT DOCUMENTS

| | | |
|---|---|---|
| EP | 1 231 279 A1 | 8/2002 |
| WO | WO 02/45523 A2 | 6/2002 |
| WO | WO 02/45524 A2 | 6/2002 |
| WO | WO 02/45524 A3 | 6/2002 |
| WO | WO 2004/098309 A1 | 11/2004 |
| WO | WO 2005/081628 A2 | 9/2005 |
| WO | WO 2006/005757 A2 | 1/2006 |

OTHER PUBLICATIONS

Tanimoto, Biosci. Biotech. Biochem., 56 (1), 140-141, 1992.*
Stewart, Nucleic Acids Research 12(9), 3895-3907, 1984.*
Jauhiainen (p. 16), "Bioactive peptides in Eolus lower the blood pressure of hypertensive subjects", Valio Foods 7 Functionals, vol. 1, 2003 (pp. 1-22).
Manso, "Angiotensin I Converting Enzyme-Inhibitory Activity of Bovine, Ovine, and Caprine kappa-Casein Macropeptides and Their Tryptic Hydrolysates", Journal of Food Protection, vol. 66, 2003, pp. 1686-1692.
Edens et al, "Extracellular Prolyl Endoprotease from *Aspergillus niger* and Its Use in he Debittering of Protein Hydrolysates", Journal of Agricultural Food Chemistry, vol. 53, Sep. 9, 2005, pp. 7950-7957.
International Search Report mailed Apr. 12, 2006 in PCT/EP2006/060198.
Brody, "Biological activities of bovine glycomacropeptide", British Journal of Nutrition (2000), 84, Suppl. 1, S39-S46.
Manso et al, "Angiotensin 1 Converting Enzyme-Inhibitory Activity of Bovine, Ovine, and Caprine k-Casein Macropeptides and Their Tryptic Hydrolysates", Journal of Food Protection, vol. 66, No. 9, 2003, pp. 1686-1692.

* cited by examiner

*Primary Examiner* — David Lukton
(74) *Attorney, Agent, or Firm* — Nixon & Vanderhye P.C.

(57) ABSTRACT

A process to produce IPP from a protein source whereby the protein source comprises a protein having the -I-P-P- sequence and having in the protein amino acid sequence at least 6 times more -I-P-P- present than -V-P-P- (molar basis) which comprises hydrolysing the protein source to liberate at least 40% of the I-P-P- sequence into the peptide IPP and whereby a proteolytic enzyme is used which cleaves at the carboxy-terminus of proline residues present in the protein source, the enzyme is preferably a proline specific endoprotease or proline specific oligopeptidase, more preferably a proline specific endoprotease, and optionally an amino peptidase.

9 Claims, 3 Drawing Sheets

BLOOD PRESSURE LOWERING PEPTIDES FROM GLYCOMACROPEPTIDE

This application is the US national phase of international application PCT/EP2006/060198 filed 23 Feb. 2006 which designated the U.S. and claims benefit of EP 05101417.3 and EP 05110236.6, dated 24 Feb. 2005 and 1 Nov. 2005, respectively, the entire content of each of which is hereby incorporated by reference.

FIELD OF THE INVENTION

The present invention relates to the production of IPP.

BACKGROUND OF THE INVENTION

Hypertension is a relatively common disease state in humans and presents a prevalent risk factor for cardiovascular diseases, kidney failure and stroke. The availability of a large array of pharmaceutical products such as calcium blockers, beta blockers, diuretics, alpha blockers, central alpha antagonists, angiotensin II antagonists and ACE inhibitors, illustrates that the underlying physiological mechanisms for hypertension are many sided.

Of the physiological mechanisms for hypertension, especially the renin-angiotensin mechanism has received a lot of scientific attention. In this mechanism, angiotensin is secreted by the liver and is cleaved by the peptidase renin to yield the biologically inactive decapeptide angiotensin I. As angiotensin I passes through the lung capillaries, another peptidase called angiotensin converting enzyme (hereinafter referred to as ACE) acts on angiotensin I by removing the last two residues of angiotensin I (His-Leu) to form the octapeptide angiotensin II. The angiotensin II octapeptide exhibits strong vasoconstricting activity and therefore raises blood pressure. ACE inhibition leading to lower levels of the angiotensin II prevents vasoconstriction and thus high blood pressures.

Apart from cleaving angiotensin I, ACE can also hydrolyse bradykinin, a nonapeptide also participating in blood pressure regulation. In the latter mechanism ACE inhibition leads to increased bradykinine levels which promote vasodilatation and lower blood pressure as well. Inhibiting ACE thus leads to blood pressure lowering effects via at least two separate mechanisms.

It is also known that the octapeptide angiotensin II stimulates the release of aldosterone by the adrenal cortex. The target organ for aldosterone is the kidney where aldosterone promotes increased reabsorption of sodium from the kidney tubules. Also via this third mechanism ACE inhibition reduces blood pressure but in this case by diminishing sodium reabsorption.

Because of its multiple physiological effects, inhibiting the proteolytic activity of ACE is an effective way of depressing blood pressure. This observation has resulted in a number of effective pharmaceutical blood pressure lowering products such as captopril and enalapril (Ondetti, M. A. et al., 1977, Science, Washington D.C., 196, 441-444).

Because hypertension is a relatively common disease state it would be advantageous to counteract this undesirable result of modern life style with mildly active natural ingredients. Especially mildly active natural ingredients that can be incorporated into food or beverage products because such products are consumed on a regular basis. Alternatively such mildly active natural ingredients could be incorporated into dietary supplements. During the last decades it has been discovered that specific peptides present in fermented milk have an ACE inhibiting capacity and can induce blood pressure reductions in hypertensive subjects. Nowadays numerous in vitro and a few animal trials have demonstrated ACE inhibiting effects of different peptides obtained from a variety of protein sources. Although in vitro ACE inhibition assays have revealed many different peptide sequences, it has to be emphasized that ACE inhibiting peptides need to circulate in the blood to exert an in vivo effect. The implication is that efficacious ACE inhibiting peptides should resist degradation by the gastrointestinal proteolytic digestion system and should remain intact during a subsequent transport over the intestinal wall.

A structure-function study of the various ACE inhibiting peptides has suggested that they often posses a Pro-Pro, Ala-Pro or Ala-Hyp at their C-terminal sequence (Maruyama, S. and Suzuki, H., 1982; Agric Biol Chem., 46(5): 1393-1394). This finding is partly explained by the fact that ACE is a peptidyl dipeptidase (EC3.4.15.1) unable to cleave peptide bonds involving proline. Thus from tripeptides having the structure Xaa-Pro-Pro the dipeptide Pro-Pro cannot be removed because the Xaa-Pro bond cannot be cleaved. It is therefore conceivable that if present in relatively high concentrations, tripeptides having the Xaa-Pro-Pro structure will inhibit ACE activity. As not only ACE but almost all proteolytic enzymes have difficulties in cleaving Xaa-Pro or Pro-Pro bonds, the notion that the presence of (multiple) proline residues at the carboxyterminal end of peptides results in relatively protease resistant molecules is almost self-evident. Similarly peptides containing hydroxyproline (Hyp) instead of proline are relatively protease resistant. From this it can be inferred that peptides carrying one or more (hydroxy)proline residues at their carboxyterminal end are likely to escape from proteolytic degradation in the gastrointestinal tract. These conclusions will help us to understand the remarkable in vivo blood pressure lowering effect of specific ACE inhibiting peptides: not only do they meet the structural requirements for ACE inhibition, they also resist degradation by the gastrointestinal proteolytic digestion system and remain intact during a subsequent transport over the intestinal wall.

Strong ACE inhibiting activities have been reported for the tripeptides Leu-Pro-Pro (JP02036127), Val-Pro-Pro (EP 0 583 074) and Ile-Pro-Pro (J. Dairy Sci., 78:777-783 1995)). Initially all ACE inhibiting peptides were characterized on the basis of their in vitro effect on ACE activity and the tripeptides Ile-Pro-Pro (hereinafter referred to as IPP) Val-Pro-Pro (hereinafter referred to as VPP) and Leu-Pro-Pro (hereinafter referred to as LPP) stood out because of their strong ACE inhibiting effect resulting in relatively low IC50 values. Later on the presumed antihypertensive effects of the tripeptides VPP as well as IPP could be confirmed in spontaneously hypertensive rats (Nakamura et al., J. Dairy Sci., 78:12531257 (1995)). In these experiments the inhibitory tripeptides were derived from lactic acid bacteria fermented bovine milk. During the milk fermentation the desirable peptides are produced by proteinases produced by the growing lactic acid bacteria. A drawback of this fermentative approach is that lactic acid bacteria are living organisms for which the type and quantity of excreted enzymes are difficult to control. The production of the ACE inhibiting peptides is therefore hardly reproducible and it is also unlikely that the optimal set of enzymes is being produced to ensure the maximal yield of the required peptides. Also the required fermentation times are relatively long which in combination with the low yields implies an unfavorable cost structure for the bioactive peptides. Moreover a fermented product is less suitable for direct incorporation into a.o. solid foods and creates strict organoleptic limitations. The poor palatability of such fermented milk products and the many processing difficulties encountered during the recovery of ACE inhibiting peptides from such fermented broths have been described in U.S. Pat. No. 6,428,812. Despite these disadvantages fermented milk products have been put to practical application as an orally administered vasodepressor. ACE inhibiting peptides have been concentrated from fermented milk products by electrodialysis, hollow fiber membrane dialysis or chromatographic methods to enable their marketing in the form of concentrated dietary supplements like tablets or lozenges.

The above mentioned drawbacks of the fermentative production route were recognized in a.o. patent applications WO 01/68115 and EP 1 231 279. In the latter application a purely enzymatic process is described to recover the tripeptides Val-Pro-Pro and Ile-Pro-Pro from milk casein. The application claims a method for producing these tripeptides by digesting material containing a milk casein with a proteinase and a peptidase via an intermediate peptide. Each of these enzyme incubations may take as long as 12 hours and take place under conditions that favor outgrowth of microbial contaminants. Prior to incubation with the peptidase, the intermediate peptide is preferably purified and high end concentrations of ACE inhibiting peptides can only be obtained after an additional chromatographic purification step of the intermediate peptide.

SUMMARY OF THE INVENTION

In the scientific literature many different peptides and hydrolysates have been correlated with blood pressure lowering effects. Moreover, many physiological mechanisms are known to be involved in blood pressure regulation. According to the present invention the peptides and the physiological mechanisms involved are minimised by selecting a suitable protein substrate which after hydrolysis will result in a peptide fraction having IPP as the main blood pressure lowering component. We have found that for such a peptide fraction kappa casein and more preferably the glycomacropeptide (GMP) from kappa-casein forms a preferred starting point. In the blood pressure lowering peptide mixture or fraction thus generated especially IPP plays an important role. In contrast to the prior art hydrolysis processes which result in mixtures of IPP, VPP and many other potentially bioactive peptides, the present process is directed towards the production of IPP thereby preventing for example the production of VPP. According to the present invention preferably proteins with a molecular weight below 20 kDa, preferably below 10 kDa comprising an -I-P-P- sequence in their amino acid sequence are used as starting proteins. As mentioned above GMP is the preferred substrate protein. GMP can be obtained from kappa-casein as described herein below. Cow's milk is the preferred origin of kappa-casein. Milk from other mammalians can also be used, for example milk from goats; if the GMP part of the kappa casein molecule comprises an -IPP- sequence. Because not all kappa caseins can be cleaved by the bovine chymosin, obtaining the GMP part may require the use of a more appropriate clotting enzyme.

The present invention discloses the use of proteins (or mixture of proteins or peptides) having in their amino acid sequences at least 6 times more -I-P-P- present than -V-P-P. Preferably the -V-P-P- sequence is absent in the protein or peptide sequence (or in the sequence of the protein or peptide mixtures used as the substrate for the hydrolysis). A preferred protein source is a protein or peptide which is free of -V-P-P- or a mixture of proteins or peptides comprising said protein which is free of -V-P-P- This mixture therefore preferably comprises at least 50%, more preferably at least 80%, still more preferably at least 90%, and most preferably at least 95% (w/w) of protein(s or peptides which are free of -V-P-P-. More preferably the -V-P-P- sequence is part of a -P-V-P-P- (SEQ ID NO: 1) or -A-V-P-P- (SEQ ID NO: 2) sequence.

A preferred example of such a protein is GMP (glycomacropeptide obtainable from bovine milk.

It is an object of the present invention to provide the blood pressure lowering peptide IPP in a pure state, i.e. without significant amounts of contamination by the peptide VPP.

It is another object of the present invention to provide the blood pressure lowering peptide IPP in a highly concentrated form without the use of expensive purification steps.

It is yet another object of the present invention to provide the blood pressure lowering peptide IPP in a non-bitter formulation. This non-bitter formulation has preferably a bitter intensity of 2 or less as defined in Example 8.

It is yet another object of the present invention to provide an enzymatic process which selectively excises IPP from the GMP part of kappa casein, preferably using a proline specific protease, more preferably a proline specific endoprotease and most preferably a proline specific endoprotease with an acid pH optimum.

It is also an object of the present invention to provide an enzymatic process which selectively produces IPP from GMP, in which the GMP preferably is first incubated with an aminopeptidase and subsequently, preferably under conditions where the aminopeptidase is not longer active, with a proline specific protease.

It is also an object of the present invention to provide a composition comprising IPP without opioid peptides being present in the same formulation.

It is also an object of the present invention to provide a composition comprising IPP in a hypoallergenic formulation.

It is also an object of the present invention to provide a composition comprising IPP in a peptide mixture with a Degree of Hydrolysis below 30%, preferably below 20%, more preferably below 15%.

It is also an object of the present invention to provide a composition comprising a hydrolysate, said hydrolysate comprises IPP and has a degree of hydrolysis below 30%, preferably below 20%, more preferably below 15%. Preferably the hydrolysate has a degree of hydrolysis of at least 1%, more preferably of at least 2%.

It is also an object of the present invention to provide a composition comprising IPP and comprising free amino levels not exceeding 10% (w/w), preferably not exceeding 7% most preferably not exceeding 3%.

It is also an object of the present invention to provide a process for the recovery of the GMP part of kappa casein from acid precipitated casein.

Moreover the present invention provides the use of the composition of the present invention or to the use the composition produced by the present process as a nutraceutical, preferably a medicament, for the manufacture of a nutraceutical, preferably a medicament, for the improvement of health or the prevention and/or treatment of diseases or for the manufacture of a nutraceutical preferably a medicament for the treatment or prevention of diseases such as high blood pressure (hypertension), heart failure, pre-diabetes or diabetes, obesity, impaired glucose tolerance or stress.

Preferably the composition of the invention is in the form of a dietary supplement, in the form of a personal care application including a topical application in the form of a lotion, gel or an emulsion or as a food, feed or pet food ingredient.

The composition of the invention can also be used for the manufacture of a functional food product for prevention of obesity or for body weight control or for the manufacture of a functional food product for the cardiovascular health maintenance, preferably the cardiovascular health maintenance comprises the inhibition of angiotensin-converting enzyme or the control of blood cholesterol levels.

The composition of the invention can be used in a functional food product capable of providing a health benefit to the consumer thereof, said health benefit is preferably selected from the prevention of obesity, body weight control and cardiovascular health maintenance.

This functional food product comprises preferably one or more B-vitamins or 3 to 25 wt % sterol.

The invention also provides a process to prepare a food product, beverage product or dietary supplement comprising production of a composition of the invention or produced by the process of the invention and incorporation of said composition into a food product, beverage product or dietary supplement.

Preferably this food product, beverage product or dietary supplement is selected from the group of margarines, spreads, butter, dairy products or whey containing beverages, preferably yoghurt or milk based products such as yoghurt or milk.

DETAILED DESCRIPTION OF THE INVENTION

The present invention relates to a process in which the peptide IPP is generated in high yields from preferably a small molecular weight protein having a high amount of -I-P-P- compared to -V-P-P- in its amino acid sequence. Preferably kappa casein more preferably the GMP fraction of kappa-casein is used. The process comprises preferably a single enzyme incubation step. Although the process according to the invention is highly specific towards the protein substrate to be used, a variety of proteolytic enzyme preparations can be used to obtain the blood pressure lowering activity in a relatively pure state. Suitable proteolytic enzyme preparations ranging from a single enzyme to complex enzyme mixtures can be used. Preferably a single enzyme is used which cleaves at the carboxy terminus of proline, preferably this enzyme is a proline specific protease or a proline specific oligopeptidase. Preferably the substrate molecule incorporates an -A-I-P-P- (SEQ ID NO: 3) or an -P-I-P-P- (SEQ ID NO: 4) sequence. Also a proline specific endoprotease, in combination with a suitable aminopeptidase can be used. In the latter case the GMP containing fraction is preferably first incubated under preferably near neutral conditions for example pH 5 to 8 with the aminopeptidase. This approach also allows the use of substrates incorporating an -X-I-P-P- sequence in which X can represent any amino acid residue. Preferably after inactivation of the aminopeptidase or under pH conditions where the aminopeptidase is not active, the N-terminally truncated GMP molecule is incubated with the proline specific protease. Preferably the protease which cleaves at the carboxyterminus of proline, such as the proline specific endoprotease, as well as the aminopeptidase activity are free from any contaminating endoprotease activities. Preferably the protease which cleaves at the carboxyterminus of proline such as the proline specific endoprotease, as well as the aminopeptidase activity are free from contaminating carboxypeptidase activities. Proline specific endo protease which is free from contaminating endoprotease activity is an enzyme preparation having preferably an ProI Spec act/Endo ratio of more than 1, more preferable more than 100. Aminopeptidase activity which is free from contaminating endoprotease activity is an enzyme preparation having preferably an AP/Endo ratio of at least 0.1, more preferable at least 0.5 and most preferable at least 1.

Proline specific endoprotease which is free for contaminating carboxyl peptidase activity is an enzyme preparation having preferably an Pro Spec act/CPD ratio of at least 1, more preferable of at least 10.

Amino peptidase activity which is free from contaminating carboxyl peptidase activity is an enzyme preparation having preferable an AP/CPD of at least 0.1, more preferable of at least 0.3. The above mentioned ratios are determined as described in Example 5.

Preferably at least 20%, more preferably at least 40%, or still more preferably at least 60% and most preferably at least 70% of -I-P-P- sequences present in the protein sequence is converted into the peptide IPP. The proline specific protease is preferably capable of hydrolyzing large protein molecules like the substrate protein itself. The process according to the invention has in general an incubation time of less than 24 hours, preferably the incubation time is less than 10 hours and more preferably less than 4 hours. The incubation temperature is in general higher than 30° C., preferably higher than 40° C. and more preferably higher than 50° C. Another aspect of the present invention is a process to purify the IPP containing peptide mixture by decanting, centrifugation or by filtration to form the soluble hydrolysate.

The present invention further discloses
a peptide composition comprising between 1 and 5 mg IPP/g (on dry matter and on protein), or between 20 and 50 mg IPP/g (on dry matter and on protein), and
a peptide composition comprising 15-90% (wt dry matter) peptides containing and at least 20 mg IPP/g (on dry matter and on protein), preferably 20 to 100 mg IPP/g (on dry matter and on protein)

In the prior art the tripeptides IPP, VPP and LPP have been described as effective ACE inhibitors. As can be judged from known amino acid sequences, the whey proteins of bovine milk do not incorporate amino acid sequences corresponding to any of these three ACE inhibiting tripeptides. Therefore peptides IPP, VPP and LPP cannot be isolated from whey proteins. However, these peptides do occur in the casein fraction of bovine milk. For example, beta-casein encompasses the -I-P-P- (74-76), the -V-P-P- (84-86) as well as the -L-P-P- (151-153) sequence. Moreover, kappa-casein also encompasses an -I-P-P- but not the other two sequences. The IPP sequence present in kappa casein is located at position 109-110, i.e a few amino acids carboxyterminal of the unique chymosin Phe (105)-Met (106) cleavage site in kappa casein. Thus in kappa casein the -I-P-P- sequence is located on the GMP part of this molecule. The inventors have found that in enzyme dotted milk the kappa casein derived IPP entity can be found in the cheese whey and in acid dotted milk in the precipitated casein part.

Despite the fact that weight-wise kappa-casein is not an important fraction of casein, the inventors have noted that from a molecular point of view its presence is quite significant. For example. beta-casein is present in a concentration of almost 400 millimoles per cubic meter of milk and kappa-casein in a concentration of 180 millimoles per cubic meter of milk. Also in cheese whey GMP represents an important fraction. Whereas the concentration of the combined serum proteins is 320 millimoles per cubic meter, GMP is present in a concentration of 400 millimoles per cubic meter of cheese whey.

Surprisingly GMP can be easily obtained. According to the present invention GMP can be selectively liberated from acid precipitated caseins by an enzymatic treatment with chymosin under selected pH conditions. Although the isolation of GMP from cheese whey is more difficult, industrial processes are known in which GMP enriched whey fractions are obtained. These commercially available GMP enriched fractions obtained with these known processes are currently being used for various nutraceutical applications.

In the present application we describe the use of GMP as a preferred starting material for obtaining the blood pressure lowering IPP in a highly purified state.

The protein fraction of milk typically incorporates a micellar casein fraction and a solubilised whey protein fraction. Among the whey proteins beta-lactoglobuline and alpha-lactalbumine are quantitatively most important. Among the casein proteins the relatively hydrophobic alpha- and beta-caseines are quantitatively predominant. Casein micelles are kept in solution by kappa-casein. A hydrohilic part of kappa casein, the socalled glycomacropeptide (GMP), protrudes from the micellar surface hereby stabilizing the hydrophobic caseins in the aqueous solution.

According to a number of well established industrial processes, the casein fraction can be isolated from the milk, e.g. for making cheese. In one of these processes milk is acidified to selectively precipitate the casein fraction from the milk. The acid precipitated material incorporates all caseins, i.e. the alpha, beta, kappa and gamma-caseins. The non-precipitated acidified milk fraction is referred to as "whey serum". In another process milk is incubated with a milk clotting enzyme, for example calf chymosin ("rennet"). Chymosin is a protease that very selectively cleaves the Phe (105)-Met (106) peptide bond of the kappa-casein. By this reaction the hydrophilic GMP part of the kappa-casein is cleaved off which results in an immediate aggregation and precipitation of the micellar casein fraction. In this case the precipitated casein fraction is referred to as "curd". As the GMP part of the kappa casein is clipped off, in this enzymatic approach the hydrophilic GMP fragment remains in solution together with the various serum proteins forming the socalled "cheese" or "sweet" whey.

Various publications claim physiological benefits from consuming GMP-enriched milk fractions. Furthermore numerous publications exist describing cost-effective routes to isolate GMP-enriched cheese whey fractions. For example the use of ultrafiltration is described in EP 1037537 and the use of an anionic resin in U.S. Pat. No. 6,787,158.

One aspect of the present invention relates to the use of a hydrolysate of GMP as blood pressure lowering agent. We have found that the relatively high level of IPP and other peptides having a carboxyterminal proline in GMP can be associated with a blood pressure lowering effect.

By hydrolysate is meant the product that is formed by the hydrolysis of the substrate protein (protein hydrolysate or hydrolysed protein), the soluble hydrolysate being the (water) soluble fraction of the protein hydrolysate which is also described herein as soluble peptide containing composition or composition comprising soluble peptides, or a mixture of a protein hydrolysate and a soluble hydrolysate.

A "peptide" or "oligopeptide" is defined herein as a chain of at least two amino acids that are linked through peptide bonds. The terms "peptide" and "oligopeptide" are considered synonymous (as is commonly recognized) and each term can be used interchangeably as the context requires. A "polypeptide" or "protein" is defined herein as a chain comprising of more than 30 amino acid residues. All (oligo) peptide and polypeptide formulas or sequences herein are written from left to right in the direction from amino-terminus to carboxy-terminus, in accordance with common practice. The one-letter code of amino acids used herein is commonly known in the art and can be found in Sambrook, et al. (Molecular Cloning: A Laboratory Manual, 2nd, ed. Cold Spring Harbor Laboratory, Cold Spring Harbor Laboratory Press, Cold Spring Harbor, N.Y., 1989).

Opioid peptides are peptides that can bind to opiate receptors.

The internationally recognized schemes for the classification and nomenclature of all enzymes from IUMB include proteases. The updated IUMB text for protease EC numbers can be found at the internet site: http://www.chem.qmw/ac.uk/iubmb/enzyme/EC3/4/11/. In this system enzymes are defined by the fact that they catalyzes a single reaction. This has the important implication that several different proteins are all described as the same enzyme, and a protein that catalyses more than one reaction is treated as more than one enzyme. The system categorises the proteases into endo- and exoproteases. Endoproteases are those enzymes that hydrolyze internal peptide bonds, exoproteases hydrolyze peptide bonds adjacent to a terminal α-amino group ("aminopeptidases"), or a peptide bond between the terminal carboxyl group and the penultimate amino acid ("carboxypeptidases"). The endoproteases are divided into sub-subclasses on the basis of catalytic mechanism. There are sub-subclasses of serine endoproteases (EC 3.4.21), cysteine endoproteases (EC 3.4.22), aspartic endoproteases (EC 3.4.23), metalloendoproteases (EC 3.4.24) and threonine endoproteases (EC 3.4.25).

The aminopeptidases are in class 3.4.11. Sub-classification is on the basis of the relative efficiency with which the 20 different amino acids are removed. Aminopeptidases with a narrow and a broad specificity can be distinguished. Aminopeptidases can sequentially remove a single amino-terminal amino acids from protein and peptide substrates. Aminopeptidases with a narrow specificity exhibit a strong preference for the type of amino acid residue at the P1 position that is liberated from the substrate peptide. Aminopeptidases of broad specificity are capable of releasing a range of different amino acids at the N-terminal or P1 positions (according to Schechter's nomenclature: Schechter, I. And Berger, A 1967. Biochem Biophys Res Commun 27:157-162). Carboxypeptidases can sequentially remove single carboxy-terminal amino acids from protein and peptide substrates. Comparable with the situation for the endoproteases, carboxypeptidases are divided into sub-subclasses on the basis of catalytic mechanism The serine-type carboxypeptidases are in class EC 3.4.16, the metallocarboxypeptidases in class EC 3.4.17 and the cysteine-type carboxypeptidases in class EC 3.4.18. The value of the EC list for proteases resides in providing standard terminology for the various types of protease activity and especially in the assignment of a unique identification number and a recommended name to each protease.

The GMP part of the kappa casein molecule is a polypeptide with a length of 64 amino acid residues. If all IPP is quantitatively recovered, a pure GMP preparation can yield an IPP concentration of almost 5% (w/w) without significant contaminations by either VPP or LPP. In the present application we describe several proteolytic processes to isolate the IPP tripeptide from the GMP polypeptide optionally in a single incubation step and with high yields. Therefore according to the process of the invention it is possible to obtain a composition comprising IPP, whereby the IPP concentration is high enough to be used directly or directly after a simple purification step so without the need of complex and costly purification process such as chromatographic isolation or purification.

According to a first proteolytic process the isolated GMP molecule is incubated with complex microbial protease enzyme preparations like Sumizyme FP (Shin Nihon) or Flavourzyme (NOVO) or Umamizyme (Amano). Sumizyme FP, Flavourzyme and Umamizyme are enzyme preparations containing various endoproteolytic enzymes plus exoproteolytic activities such as aminopeptidases and carboxypeptidases. By a careful selection of the enzyme dosage and the pH conditions we have been able to obtain the IPP tripeptide in a single incubation step using either the Sumizyme FP or the Flavourzyme preparation. However, a disadvantage of this first proteolytic strategy is that a variety of different peptides can be formed by the various enzymatic activities present. Moreover, relatively high amounts of free amino acids are generated that will impart brothy off-tastes on the final IPP containing product unless the hydrolysate is further purified.

According to a second proteolytic process the isolated GMP molecule is incubated with a proline specific oligopeptidase (EC 3.4.21.26) or a proline specific endopeptidase. In this approach the unique specificity of these two types of enzymes is advantageously used. Both types of proline specific proteases preferably hydrolyse peptide bonds C-terminal of proline residues. However, an inherent side activity of these two enzymes is directed towards hydrolysing C-terminal of alanine residues. As the -I-P-P- sequence as present in GMP is N-terminally preceded by an alanine residue, incubation of GMP with a pure proline specific oligopeptidase or a pure proline specific endopeptidase directly yields IPP. Important advantage of this route is that high IPP yields are obtained without the concomitant generation of a large number of other peptides that can lead to very bitter off-tastes and even exert undesired bioactivities. Furthermore almost no free amino acids are generated during this process so that a bland tasting product is obtained with a high concentration of IPP.

According to a further proteolytic process the isolated GMP molecule is first incubated with an aminopeptidase to remove the GMP N-terminal amino acids (Met and Ala) preceding the IPP sequence in GMP. Only after this incubation the proline specific protease is added to the reaction mixture to release the IPP peptide. Preferably the aminopeptidase is not longer active during or after the incubation with the proline specific protease. We have found that this approach leads to higher IPP yields and yet, does not lead to off-taste generation and hardly contributes to the amount of free amino acids present in the end product. Moreover, IPP is present at a high amount relative too other peptides, especially relative to tripeptides. The IPP prepared can be further separated from the larger peptides. As aminopeptidases can sequentially remove amino acids from the N-terminal side of peptides, an aminopeptidolytic enzyme activity is required that can efficiently liberate the methionine ("M") and the alanine ("A") residues preceding the IPP sequence. The I-P and P-P peptide bonds present in IPP tripeptides were found to resist enzymatic cleavage, and after incubation of an intact GMP molecule such an aminopeptidolytic activity will truncate the N-terminus of the GMP molecule to start with the sequence IPP.

A commercial enzyme preparation having the desired aminopeptidase activity is Corolase LAP (AB Enzymes). Corolase LAP represents a relatively pure, cloned and overexpressed leucine aminopeptidase activity from *Aspergillus*. Because this preparation lacks non-specified endoproteolytic and carboxypeptidolytic activities, undesired cleavage of the GMP substrate molecule is prevented. Another cloned and overexpressed aminopeptidase with a relatively broad specificity is aminopeptidase from *A. niger* (SEQ ID 171 of WO 02/068623).

Finally we have noted that GMP is also advantageously used in processes in which IPP is produced by a fermentative route. As illustrated in the Examples, the incubation of GMP with specific lactobacilli yields IPP without the generation of the off-tastes that are characteristic for whole milk fermentations.

All the above mentioned aspects are of particular importance as it allows the production of a highly standardized product without unwanted bio-activities or taste or odor profiles. Such a highly standardized product can be incorporated without subsequent purification steps in various food applications or in concentrated dietary products like tablets or lozenges. Highly standardized products containing even higher IPP concentrations, e.g. to produce smaller tablets or lozenges, can be obtained by a selective removal of peptides other than IPP. Such a removal of peptides without significant blood-pressure lowering activities can be accomplished e.g. by precipitating these non-active peptides followed by an (ultra) filtration or a decantation step. In yet another approach, the concentration of the bioactive ingredients can be further increased by subsequent purification in which use is made of the very hydrophobic character of peptide IPP. These purification methods include nanofiltration, extraction for example with butanol followed by evaporation/precipitation or contacting the acidified hydrolysate as obtained with binders like active carbon or chromatographic resins from, for example, the Amberlite XAD range (Rohm). Also butyl-sepharose resins as supplied by, for example, Pharmacia can be used. Desorption of the blood pressure lowering peptides from such materials can be done with organic solvents like methanol/ethanol mixtures or with propanol. Furthermore supercritical extraction using $CO_2$ or $N_2O$ can be used to obtain highly purified bioactive peptides.

In EP 1 231 279 a purely enzymatic process is described to recover the tripeptides VPP and IPP from milk casein. The application claims a method for producing tripeptides by digesting a material containing a milk casein with a proteinase and a peptidase via a socalled "intermediate peptide" selected from the group consisting of a peptide containing a sequence -V-P-P- but containing no Pro other than those in this sequence as well as a peptide containing a sequence -I-P-P- but containing no Pro other than those in this sequence. As described in the Examples of EP 1 231 279 the method involves a two-step process. First the intermediate peptides encompassing either VPP or IPP are produced. This is done by incubating casein with a suitable proteinase. According to one of the Examples at 37 degrees C. for a 12 hours period. Then the proteinase used is inactivated by heating this first hydrolysate to 100 degrees C. for 3 minutes and, after cooling down again, another enzyme preparation (in fact a preparation with exoproteolytic activity) is added. After another 12 hours incubation at 37 degrees C. with this other enzyme preparation the presence of the tripeptides VPP and IPP can be demonstrated. To obtain higher yields of these ACE inhibiting peptides, EP 1 231 279 further suggests to purify and concentrate the intermediate peptide prior to exposure to the exoproteolytic activity. EP 1 231 279 also suggests that after obtaining the intermediate peptide and before the intermediate peptide is contacted with the peptidase in the procedure various operations may optionally be performed such as the removal of the unreacted protein by e.g. centrifugation at 5000 to 20000 rpm for 3 to 10 minutes. So the complex mixture of the desired tripeptides is obtained in an industrially rather unwieldy two-step enzymatic process. As each of the enzyme incubations may take as long as 12 hours at pH 4.5 to 7.0 and at the temperature of 25 to 50 degrees C., it is evident that this procedure is also unacceptable from a microbiological point of view. These long incubation times combined with low incubation temperature of 25 to 50° C. may easily result in infections of the protein containing solution.

Upon a comparison with the methods described in EP 1 231 279, the elegance of the inventive steps specified in the present application becomes clear. First of all, the present application describes the use of only a GMP fragment of kappa casein. As a result, only IPP will be released and many other, potentially very bitter peptides known to be encompassed by casein, are not generated. Secondly, the incubation according to the present invention using the proline specific protease is carried out by a single, pure enzyme in a single incubation step. Because of the very selective cleavage pattern of the proline specific protease, which is inherent to this particular endoprotease, the desired IPP peptide is immediately released concomitantly with a very limited number of other peptides. Surprisingly no "intermediate peptide" as mentioned in EP 1 231 279 is formed. Thirdly, the incubation according to the present invention in which the GMP casein fragment is first incubated with a pure aminopeptidase followed by an incubation with the proline specific protease is essentially different from the route described in EP 1 231 279 and yet releases IPP with a high efficiency and with minimal levels of contaminating peptides and free amino acids. The preferred incubation starts with an aminopeptidase (a "peptidase" according to EP 1 231 279) instead of a proteinase and does not yield an "intermediate peptide". In the following step an endoprotease instead of a proteinase is used and again no "intermediate peptide" is formed.

Despite all disadvantages mentioned for prior art products, fermented milk products have been put to practical application as an orally administered vasodepressor. ACE inhibiting peptides also have been concentrated from fermented milk products by electrodialysis, hollow fiber membrane dialysis or chromatographic methods to enable their marketing in the form of concentrated dietary supplements like tablets or lozenges.

It is an object of the present invention to provide the peptide IPP in a pure state, i.e. without a significant contamination by the peptides like VPP or LPP.

It is another object of the present invention to provide the peptide IPP in a highly concentrated form without the use of expensive purification steps.

It is yet an object of the present invention to provide the blood pressure lowering peptide IPP in a non-bitter formulation.

The present invention relates to a peptide containing composition for use as a nutraceutical, preferably a medicament. The invention also relates to the use of present peptide containing composition as a nutraceutical preferably a medicament, to the use of present peptide containing composition for the manufacture of a nutraceutical preferably a medicament, to the use of the present peptide containing composition for the improvement of health or the prevention and/or treatment of diseases, to the use of the present peptide containing composition for the manufacture of a nutraceutical preferably a medicament, to the use of the present peptide containing composition for the treatment of cardiovascular diseases such as hypertension and heart failure, to the use of the present peptide containing composition for the treatment of pre-diabetes or diabetes, to the use of the present peptide containing composition for the treatment or prevention of obesity, to the use of the present peptide containing composition to increase plasma insulin or to increase the sensitivity for plasma insulin, to the use of the present peptide containing composition to increase plasma insulin or to increase the sensitivity for plasma insulin of type 2 diabetes or pre-diabetes, to the use of the present peptide containing composition to lower post-prandial glucose concentrations in blood of type 2 diabetes or pre-diabetes, to the use of the present peptide containing composition to increase post-prandial insulin secretion in blood of type 2 diabetes or pre-diabetes, to the use of the present peptide containing composition wherein the present peptide containing composition is in the form of a dietary supplement, to the use of the present peptide containing composition for the manufacture of a functional food product for the therapeutic treatment of the effects of stress, to the use of the present peptide containing composition in topical application preferably in personal care application and to the use of the present peptide containing composition in feed and pet food.

Furthermore the present invention relates to a method of treatment of type 1 and 2 diabetes, and for the prevention of type 2 diabetes in those individuals with pre-diabetes, or impaired glucose tolerance (IGT) which comprises administering to a subject in need of such treatment the present peptide containing composition and to a method of treatment of people that suffer of hypertension or heart failure or the prevention thereof which comprises administering to a subject in need of such treatment the present peptide containing composition and thus, exhibit blood pressure lowering effects. Inhibition of ACE results in reduced vasoconstriction, enhanced vasodilation, improved sodium and water excretion, which in turn leads to reduced peripheral vascular resistance and blood pressure and improved local blood flow. Thus, the present hydrolysates, comprising peptide, are particularly efficacious for the prevention and treatment of diseases that can be influenced by ACE inhibition, which include but are not limited to hypertension, heart failure, angina pectoris, myocardial infarction, stroke, peripheral arterial obstructive disease, atherosclerosis, nephropathy, renal insufficiency, erectile dysfunction, endothelial dysfunction, left ventricular hypertrophy, diabetic vasculopathy, fluid retention, and hyperaldosteronism. The compositions may also be useful in the prevention and treatment of gastrointestinal disorders (diarrhea, irritable bowel syndrome), inflammation, diabetes mellitus, obesity, dementia, epilepsy, geriatric confusion, and Meniere's disease. Furthermore, the compositions may enhance cognitive function and memory (including Alzheimer's disease), satiety feeling, limit ischemic damage, and prevent reocclusion of an artery after by-pass surgery or angioplasty.

Diabetes mellitus is a widespread chronic disease that hitherto has no cure. The incidence and prevalence of diabetes mellitus is increasing exponentially and it is among the most common metabolic disorders in developed and developing countries. Diabetes mellitus is a complex disease derived from multiple causative factors and characterized by impaired carbohydrate, protein and fat metabolism associated with a deficiency in insulin secretion and/or insulin resistance. This results in elevated fasting and postprandial serum glucose concentrations that lead to complications if left untreated. There are two major categories of the disease, insulin-dependent diabetes mellitus (IDDM, T1DM) and non-insulin-dependent diabetes mellitus (NIDDM, T2DM). T1DM=type 1 diabetes mellitus. T2DM=type 2 diabetes mellitus.

T1DM and T2DM diabetes are associated with hyperglycemia, hypercholesterolemia and hyperlipidemia. The absolute insulin deficiency and insensitivity to insulin in T1DM and T2DM, respectively, leads to a decrease in glucose utilization by the liver, muscle and the adipose tissue and to an increase in the blood glucose levels. Uncontrolled hyperglycemia is associated with increased and premature mortality due to an increased risk for microvascular and macrovascular diseases, including nephropathy, neuropathy, retinopathy, hypertension, stroke, and heart disease. Recent evidence showed that tight glycemic control is a major factor in the prevention of these complications in both T1DM and T2DM. Therefore, optimal glycemic control by drugs or therapeutic regimens is an important approach for the treatment of diabetes.

Therapy of T2DM initially involves dietary and lifestyle changes, when these measures fail to maintain adequate glycemic control the patients are treated with oral hypoglycemic agents and/or exogenous insulin. The current oral pharmacological agents for the treatment of T2DM include those that potentate insulin secretion (sulphonylurea agents), those that improve the action of insulin in the liver (biguanide agents), insulin-sensitizing agents (thiazolidinediones) and agents which act to inhibit the uptake of glucose α-glucosidase inhibitors). However, currently available agents generally fail to maintain adequate glycemic control in the long term due to progressive deterioration of hyperglycemia, resulting from progressive loss of pancreatic cell function. The proportion of patients able to maintain target glycemia levels decreases markedly over time necessitating the administration of additional/alternative pharmacological agents. Furthermore, the drugs may have unwanted side effects and are associated with high primary and secondary failure rates. Finally, the use of hypoglycemic drugs may be effective in controlling blood glucose levels, but may not prevent all the complications of diabetes. Thus, current methods of treatment for all types of diabetes mellitus fail to achieve the ideals of normoglycemia and the prevention of diabetic complications. Therefore, although the therapies of choice in the treatment of T1DM and T2DM are based essentially on the administration of insulin and of oral hypoglycemic drugs, there is a need for a safe and effective nutritional supplement with minimal side effects for the treatment and prevention of diabetes. Many patients are interested in alternative therapies which could minimize the side effects associated with high-dose of drugs and yield additive clinical benefits. Patients with diabetes mellitus have a special interest in treatment considered as "natural" with mild anti-diabetic effects and without major side effects, which can be used as adjuvant treatment. T2DM is a progressive and chronic disease, which usually is not recognized until significant damage has occurred to the pancreatic cells responsible for producing insulin (β-cells of islets of Langerhans). Therefore, there is an increasing interest in the development of a dietary supplement that may be used to prevent β-cell damage and thus, the progression to overt T2DM in people at risk especially in elderly who are at high risk for developing T2DM. Protection of pancreatic β-cells may be achieved by decreasing blood glucose and/or lipid levels as glucose and lipids exert damaging effects on β-cells. The reduction of blood glucose levels can be achieved via different mechanisms, for example by enhancing insulin sensitivity and/or by reducing hepatic glucose production. The reduction of blood lipid levels can also be achieved via different mechanisms, for example by enhancing lipid oxidation and/or lipid storage. Another possible strategy to protect pancreatic β-cells would be to decrease oxidative stress. Oxidative stress also causes β-cell damage with subsequent loss of insulin secretion and progression to overt T2DM.

Therefore, T2DM is a complicated disease resulting from coexisting defects at multiple organ sites: resistance to insulin action in muscle and adipose tissues, defective pancreatic insulin secretion, unrestrained hepatic glucose production. Those defects are often associated with lipid abnormalities and endothelial dysfunction. Given the multiple pathophysiological lesions in T2DM, combination therapy is an attractive approach to its management.

The present invention relates to novel nutraceutical compositions comprising the peptide containing composition of the present invention. The nutraceutical compositions comprising the peptide containing composition of the present invention can also comprise unhydrolysed proteins and carbohydrates as the active ingredients for the treatment or prevention of diabetes mellitus, or other conditions associated with impaired glucose tolerance such as syndrome X. In another aspect the present invention relates to the use of such compositions as a nutritional supplement for the said treatment or prevention, e.g., as an additive to a multi-vitamin preparations comprising vitamins and minerals which are essential for the maintenance of normal metabolic function but are not synthesized in the body. In still another aspect, the invention relates to a method for the treatment of both type 1 and 2 diabetes mellitus and for the prevention of T2DM in those individuals with pre-diabetes, or impaired glucose tolerance (IGT) or obesity which comprises administering to a subject in need of such treatment the peptide containing composition of the present invention and protein hydrolysates or unhydrolysed proteins and/or carbohydrates.

The compositions of the present invention are particularly intended for the treatment of both T1DM and T2DM, and for the prevention of T2DM in those individuals with pre-diabetes, or impaired glucose tolerance (IGT).

It is found that the present peptide containing compositions can be used for type 2 diabetes or prediabetes, preferably to lower post-prandial glucose concentrations or to increase post-prandial insulin secretion in blood.

The compositions comprising peptide and optionally carbohydrates stimulate insulin secretion and increase glucose disposal to insulin sensitive target tissues such as adipose tissue, skeletal muscle and liver and, thus, provide synergistic effects in the treatment of diabetes mellitus.

It is generally recognised that stress-related diseases, and the negative effects of stress upon the body, have a significant impact upon many people. In recent years the effects of stress, and its contribution towards various the development of various diseases and conditions, has gained wider acceptance in the medical and scientific community. Consumers are now becoming increasingly aware of these potential problems and are becoming increasingly interested in reducing or preventing the possible negative impact of stress on their health.

It is a further object of the invention to provide a food product, or an ingredient which can be incorporated therein, which is suitable for use in helping the body deal with the effects of stress.

It is a further object to provide a food product comprising the present peptide containing composition which provides a health benefit, such as helping the body deal with the negative effects of stress.

The term nutraceutical as used herein denotes the usefulness in both the nutritional and pharmaceutical field of application. Thus, the novel nutraceutical compositions can find use as supplement to food and beverages, and as pharmaceutical formulations or medicaments for enteral or parenteral application which may be solid formulations such as capsules or tablets, or liquid formulations, such as solutions or suspensions. As will be evident from the foregoing, the term nutraceutical composition also comprises food and beverages comprising the present peptide containing composition and optionally carbohydrate as well as supplement compositions, for example dietary supplements, comprising the aforesaid active ingredients.

The term dietary supplement as used herein denotes a product taken by mouth that contains a "dietary ingredient" intended to supplement the diet. The "dietary ingredients" in these products may include: vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms, such as a bar, but if they are, information on the label of the dietary supplement will in general not represent the product as a conventional food or a sole item of a meal or diet.

A multi-vitamin and mineral supplement may be added to the nutraceutical compositions of the present invention to obtain an adequate amount of an essential nutrient missing in some diets. The multi-vitamin and mineral supplement may also be useful for disease prevention and protection against nutritional losses and deficiencies due to lifestyle patterns and common inadequate dietary patterns sometimes observed in diabetes. Moreover, oxidant stress has been implicated in the development of insulin resistance. Reactive oxygen species may impair insulin stimulated glucose uptake by disturbing the insulin receptor signaling cascade. The control of oxidant stress with antioxidants such as α-tocopherol (vitamin E) ascorbic acid (vitamin C) may be of value in the treatment of diabetes. Therefore, the intake of a multi-vitamin supplement may be added to the above mentioned active substances to maintain a well balanced nutrition.

Furthermore, the combination of the present peptide containing composition with minerals such as magnesium ($Mg^{2+}$), Calcium ($Ca^{2+}$) and/or potassium ($K^+$) may be used for the improvement of health and the prevention and/or treatment of diseases including but not limited to cardiovascular diseases and diabetes.

In a preferred aspect of the invention, the nutraceutical composition of the present invention contains the present peptide containing compositions. IPP is present in the composition according to the invention in an amount to provide a daily dosage from about 0.001 g per kg body weight to about 1 g per kg body weight of the subject to which it is to be administered. A food or beverage suitably contains about 0.05 g per serving to about 50 g per serving of IPP. If the nutraceutical composition is a pharmaceutical formulation such formulation may contain IPP, in an amount from about 0.001 g to about 1 g per dosage unit, e.g., per-capsule or tablet, or from about 0.035 g per daily dose to about 70 g per daily dose of a liquid formulation. The present peptide containing compositions suitably are present in the composition according to the invention in an amount to provide a daily dosage from about 0.01 g per kg body weight to about 3 g per kg body weight of the subject to which it is to be administered. A food or beverage suitably contains about 0.1 g per serving to about 100 g per serving of protein hydrolysates. If the nutraceutical composition is a pharmaceutical formulation such formulation may contain peptide containing compositions in an amount from about 0.01 g to about 5 g per dosage unit, e.g., per capsule or tablet, or from about 0.7 g per daily dose to about 210 g per daily dose of a liquid formulation.

In yet another preferred aspect of the invention a composition comprises the present peptide as specified above and optionally carbohydrates. Carbohydrates suitably are present in the composition according to the invention in an amount to provide a daily dosage from about 0.01 g per kg body weight to about 7 g per kg body weight of the subject to which it is to be administered. A food or beverage suitably contains about 0.5 g per serving to about 200 g per serving of carbohydrates. If the nutraceutical composition is a pharmaceutical formulation such formulation may contain carbohydrates in an amount from about 0.05 g to about 10 g per dosage unit, e.g., per capsule or tablet, or from about 0.7 g per daily dose to about 490 g per daily dose of a liquid formulation.

Dosage Ranges (for a 70 kg Person)
IPP: 0.005-70 g/day (each)
Protein hydrolysates: 0.07-210 g/day
Unhydrolysed proteins: 0.07-210 g/day
Carbohydrates: 0.1490 g/day It is an object of the invention to provide an edible material which can be used to provide health benefits to a subject consuming it. It is yet a further object to provide such an edible material which can conveniently be ingested either in isolated form or incorporated into a food product.

It is a further object of the invention to provide a food product, or an ingredient which can be incorporated therein, which is suitable for use in body weight control programmes.

It is a further object of the invention to provide a food product, or an ingredient which can be incorporated therein, which is suitable for helping to maintain cardiovascular health, e.g. through ACE inhibition.

It is a further object of the invention to provide a food product, or an ingredient which can be incorporated therein, which have acceptable stability and/or organoleptic properties, in particular good taste, such as an absence of or an acceptable level of bitterness.

It is a further object to provide a food product having a high concentration of an ingredient which provides a health benefit, such as aiding the prevention of obesity/body weight control and/or helping maintain cardiovascular health.

Surprisingly, one or more of these objects is attained according to the invention by the use of the present peptide containing composition for the preparation of a food product which provides a health benefit upon consumption.

According to a first aspect the present invention provides the use of the present peptide containing composition for the manufacture of a functional food product for the prevention of obesity or body weight control.

According to a second aspect the present invention provides the use of the present peptide containing composition for the manufacture of a functional food product for cardiovascular health maintenance.

It is especially preferred according to the present invention that cardiovascular health maintenance comprises the inhibition of angiotensin-converting (ACE) enzyme and/or the control of blood glucose levels.

According to a third aspect the present invention provides a functional food product capable of providing a health benefit to the consumer thereof, said health benefit selected from the prevention of obesity, body weight control and cardiovascular health maintenance and comprising the present peptide containing composition.

A further advantage of the peptide containing composition according to the present invention is that this peptide containing composition can be conveniently incorporated into food products, to produce, functional food products, without unacceptably affecting the stability and/or organoleptic properties thereof.

"Health benefit agent(s)" according to the present invention are materials which provide a health benefit, that is which have a positive effect on an aspect of health or which help to maintain an aspect of good health, when ingested, these aspects of good health being prevention of obesity, body weight control and cardiovascular health maintenance.

"Health benefit" means having a positive effect on an aspect of health or helping to maintain an aspect of good health.

"Functional food products" according to the present invention are defined as food products (including for the avoidance of doubt, beverages), suitable for human consumption, in which the peptide containing composition of the present invention is used as an ingredient in an effective amount, such that a noticeable health benefit for the consumer of the food product is obtained.

The term "comprising" where used herein is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

It is yet another object of the present invention to provide an enzymatic process which selectively excises IPP from the GMP part of kappa casein, preferably using a proline specific protease, more preferably a proline specific endoprotease and most preferably a proline specific endoprotease with an acid pH optimum.

It is also an object of the present invention to provide a process for the recovery of the GMP part of kappa casein from acid precipitated casein.

The effective blood pressure lowering peptide IPP has two proline residues at the carboxyterminal end of the peptide. As peptide bonds incorporating prolyl residues are known to resist proteolytic cleavage, the presence of two proline residues in blood pressure lowering peptides will endow such peptides with increased resistance against proteolytic degradation. This aspect increases the probability that the relevant tripeptide will escape total hydrolysis during incubation with complex enzyme preparations. Similarly IPP is likely to survive gastro-intestinal digestion so that these peptides stand a better chance of reaching the blood stream intact. To obtain peptides with at least a single but preferably multiple proline residues at their carboxyterminal end, the use of a protease that can cleave at the carboxyterminal side of proline residues offers an interesting option. Socalled prolyl oligopeptidases (EC 3.4.21.26) have the unique possibility of preferentially cleaving peptides at the carboxyl side of proline residues and, be it with a lower efficiency, at the carboxyl side of alanine. In all adequately characterized proline specific proteases isolated from mammalian as well as microbial sources, a unique peptidase domain has been identified that excludes large peptides from the enzyme's active site. In fact these enzymes are unable to degrade polypeptides containing more than about 30 amino acid residues so that these enzymes are now referred to as "prolyl oligopeptidases" (Fulop et al: Cell, Vol. 94, 161-170, Jul. 24, 1998). As a consequence these prolyl oligopeptidases require an extensive pre-hydrolysis with other endoproteases before they can exert their hydrolytic action. However, as described in WO 02/45523, even the combination of a prolyl oligopeptidase with such another endoprotease results in hydrolysates characterized by a significantly enhanced proportion of peptides with a carboxyterminal proline residue. Because of this, such hydrolysates form an excellent starting point for the isolation of peptides with in vitro ACE inhibiting effects as well as an improved resistance to gastro-intestinal proteolytic degradation. Despite these potential benefits, we are not aware of an application specifying the use of proline specific proteases for the recovery of blood pressure lowering peptides let alone for the selective production of IPP.

WO 02/45524 describes a proline specific protease obtainable from *Aspergillus niger*. The *A. niger* derived enzyme cleaves preferentially at the carboxyterminus of proline, but can also cleave at the carboxyterminus of hydroxyproline and, be it with a lower efficiency, at the carboxyterminus of alanine. WO 02/45524 also teaches that there exists no clear homology between this *A. niger* derived enzyme and the known prolyl oligopeptidases from other microbial or mammalian sources. In contrast with known prolyl oligopeptidases, the *A. niger* enzyme has an acid pH optimum. Although the known prolyl oligopeptidases as well as the *A. niger* derived enzyme are socalled serine proteases, we show in Example 1 that the *A. niger* enzyme belongs to a completely different subfamily. The secreted *A. niger* enzyme appears to be a member of family S28 of serine peptidases rather than the S9 family into which most cytosolic prolyl oligopeptidases have been grouped (Rawlings, N. D. and Barrett, A. J.; Biochim. Biophys. Acta 1298 (1996) 1-3).

In Example 2 we show the pH and temperature optima of the *A. niger* derived proline specific endoprotease in comparison with a proline specific oligopeptidase as obtained from the microorganism *Flavobacterium meningosepticum*. Aqueous solutions containing protein are highly susceptible for microbial infections, especially if kept for many hours at pH values above 5.0 and at temperatures of 50 degrees C. or below. Especially microbial toxins that can be produced during such prolonged incubation steps and are likely to survive subsequent heating steps and form a potential threat to food grade processes. Unlike the conditions described in EP 1 231 279 the process according to the present invention preferably uses an incubation temperature above 50 degrees C. In combination with the one-step enzyme process in which the enzyme incubation is carried out for a period less than 24 hours, preferably less than 8 hours, more preferably less than 4 hours, the process according to the invention offers the advantage of an improved microbiological stability.

In Example 3 we demonstrate that the *A. niger* derived enzyme preparation as used in the process of the present invention exhibits a very narrow substrate specificity meaning that no significant endoproteolytic activity other than towards peptide bonds involving a proline or an alanine residue is present. In Example 4 of the present application we show that the *Aspergillus* enzyme is not an oligopeptidase but a true endopeptidase able to hydrolyse intact proteins, large peptides as well as smaller peptide molecules without the need of an accessory endoprotease. This new and surprising finding allows us to omit the use of an accessory endoprotease so that hydrolysates with unprecedented high contents of peptides with a carboxyterminal proline residue can be generated. Furthermore the omission of an accessory endoprotease is preferred to generate a very limited number of peptides upon hydrolysing either polypeptides or oligopeptides. As a result relatively simple peptide mixtures are obtained that are characterized by the fact that most of the peptides present have a carboxyterminal proline residue.

In Example 5 we characterize the enzyme preparations used in terms of endoproteolytic, aminopeptidolytic and carboxypeptidolytic activities present. Whereas the proline specific endoprotease has negligible side-activities, the Sumizyme FP and the Flavourzyme preparations form a rich source of many different enzyme types.

In Example 6 we describe an alternative route for the isolation of GMP i.e. an isolation from commercially available caseinate. Using the proline specific endoprotease we also recover IPP from the GMP thus isolated. The fact that the *A. niger* derived enzyme does not contain significant aminopeptidase activity (cf. Example 5) strongly suggests that the IPP formed is released from the -A107-I108-P109-P110- (SEQ ID NO: 3) sequence present in kappa-caseine. Presumably the peptide bond carboxyterminal of IPP is cleaved by the main activity of the *A. niger* derived prolyl endoprotease whereas cleavage of the preceding Ala-Ile bond is accomplished by its Ala-specific side activity. Advantage of this route is that after the selective removal of the GMP, the remaining caseinate fraction can be used for alternative applications.

In Example 7 we show that both the proline specific endoprotease as well as the complex Sumizyme FP preparation can be used to liberate IPP from commercially obtained GMP. Preferably this composition comprises between 0.1 to 100 mg/g IPP (on dry matter and on protein), more preferably between 1 to 50 mg/g IPP (on dry matter and on protein) and most preferably between 2 and 35 mg/g IPP (on dry matter and on protein). We have also found that hydrolysis of GMP results in a composition comprising the tripeptide IPP and the tetrapeptide TSTP (SEQ ID NO: 5) in almost identical amounts in case proline specific endoprotease is used. Therefore the present invention also relates to a composition comprising IPP and TSTP (SEQ ID NO: 5) and whereby the molar ration of IPP:TSTP (SEQ ID NO: 5) is between 1.5 and 0.5, preferably between 1.3 and 0.7 and more preferably between 1.2 and 0.8. Preferably this composition comprises between 0.1 to 100 mg/g IPP (on dry matter and on protein), more preferably between 1 to 50 mg/g IPP (on dry matter and on protein) and most preferably between 2 and 35 mg/g IPP (on dry matter and on protein)

In Example 8 we demonstrate the organoleptical advantages of using a GMP hydrolysate.

In Example 9 we illustrate that the use of GMP also allows the preparation of IPP containing products by a fermentative approach.

Therefore the present invention results in several advantages over the prior art. Most importantly the process according to the invention generates a smaller variety of water soluble peptides and among these water soluble peptides IPP is present in major amounts. This is especially important in case a high concentration of IPP is needed in a bland tasting product. According to the present process preferably at least 20%, more preferably at least 30%, most preferably at least 40% of an -A-I-P-P (SEQ ID NO: 3) sequence present in a protein is converted into IPP.

After hydrolysis the solution can be heated. Optionally the pH of the solution can be modified or the solution can be mixed with solvents.

According to one aspect of the invention the soluble peptides, including IPP, which are formed during the hydrolysis of the protein source, are separated and optionally dried. After for example decantation, filtration or low speed centrifugation to remove the precipitate formed, the supernatants containing the biologically active soluble peptides can be recovered by for example reverse osmosis or evaporation, optionally in combination with an additional filtration step optionally followed by a spray drying step to yield an economical route for obtaining a food grade paste or powder with a high bio-activity and a good water solubility. Upon the digestion of the suitable substrate protein such as GMP by a proline specific endoprotease a white and odourless powder with a high concentration of IPP and a surprisingly low Degree of Hydrolysis is obtained.

In nutraceutical applications and food and beverage applications, hydrolysates of the inventions are advantageously used. A protein hydrolysate, an soluble hydrolysate as well as an mixture thereof can be used in a nutraceutical application, a food application or a beverage. Preferably the soluble hydrolysate is used in a nutraceutical application, a food application or a beverage because of the high content of active peptides present.

If appropriately diluted to the right tripeptide concentration, a versatile starting material with an excellent palatability is obtained suitable for endowing all kinds of foods and beverages with blood pressure lowering properties.

The peptide mixture as obtained either before or after an additional purification step, such as for example chromatography, may be used for the incorporation into food products that are widely consumed on a regular basis. Examples of such products are margarines, spreads, various dairy products such as butter or yoghurts or milk or whey containing beverages, bakery items such as cakes and cookies, liquid foods such as soups as well as candies and sweeteners and sugar lumps. As a result of the very bland taste of the IPP containing hydrolysates according to the invention, the incorporation of the hydrolysate in all kinds of beverages including bottled table water, soft drinks, sport drinks, fruit juices, lemonades and instant teas and coffees presents is possible.

A sports drink is a beverage which is supposed to rehydrate athletes, as well as restoring electrolytes, sugar, and other nutrients. Sports drinks are usually isotonic, meaning they contain the same proportions of nutrients as found in the human body. (Source: http://en.wikipedia.org/wikiSports_drink)

Energy drinks are beverages which contain (legal) stimulants, vitamins (especially B vitamins) and minerals with the intent to give the user a burst of energy. Common ingredients include caffeine, *guarana* (caffeine from the *Guarana* plant), taurine, various forms of ginseng, maltodextrin, inositol, carnitine, creatine, glucuronolactone and *ginkgo biloba*. Some may contain high levels of sugar, or glucose. Many such beverages are flavored and/or colored. (Source: http://en.wikipedia.org/wiki/Energy_drink)

A soft drink is a drink that does not contain alcohol, as opposed to hard drinks, that do. In general, the term is used only for cold beverages. Hot chocolate, tea, and coffee are not considered soft drinks. The term originally referred exclusively to carbonated drinks, and is still commonly used in this manner. (Source: http://en.wikipedia.org/wiki/Soft_drink)

Although such compositions are typically administered to human beings, they may also be administered to animals, preferably mammals, to relief hypertension. Furthermore the high concentration of blood pressure lowering peptide in the products as obtained makes these products very useful for the incorporation into dietary supplements in the form off pills, tablets or highly concentrated solutions or pastes or powders. Slow release dietary supplements that will ensure a continuous release of the peptides are of particular interest. The peptides according to the invention may be formulated as a dry powder in, for example, a pill, a tablet, a granule, a sachet or a capsule. Alternatively the peptide mixture according to the invention may be formulated as a liquid in, for example, a syrup or a capsule. The compositions used in the various formulations and containing the enzymes according to the invention may also incorporate at least one compound of the group consisting of a physiologically acceptable carrier, adjuvant, excipient, stabiliser, buffer and diluant which terms are used in their ordinary sense to indicate substances that assist in the packaging, delivery, absorption, stabilisation, or, in the case of an adjuvant, enhancing the physiological effect. The relevant background on the various compounds that can be used in combination with the peptide mixture according to the invention in a powdered form can be found in "Pharmaceutical Dosage Forms", second edition, Volumes 1, 2 and 3, ISBN 0-8247-80442 Marcel Dekker, Inc. or in Remington's Pharmaceutical Sciences, 20th edition Williams & Wilkins, P A, USA. For oral administration, tablets and capsules are preferably used which contain a suitable binding agent, e.g.

gelatine or polyvinyl pyrrolidone, a suitable filler, e.g. lactose or starch, a suitable lubricant, e.g. magnesium stearate, and optionally further additives.

A relatively new oral application form is the use of various types of gelatin capsules or gelatin based tablets.

To a further aspect of the invention, a hydrolysate is provided which is free of phenylalanine, tryptophane and tyrosine. By using GMP as starting protein, a hydrolysate is obtained that lacks phenylalanine, tryptophane and tyrosine. This makes this hydrolysate safe for individuals with phenylketonuria (PKU).

In view of the relevance of natural peptides to fight hypertension the present new and cost effective route offers an attractive starting point for mildly hypotensive alimentary or even veterinary products. Because the present route incorporates a surprisingly simple purification step, the possibilities for blood pressure lowering concentrated dietary supplements are also enlarged.

The process according to the invention can be accomplished using any proline specific oligo- or endoprotease. By proline specific oligopeptidases according to the invention or used according to the invention are meant the enzymes belonging to EC 3.4.21.26. By the proline specific endo protease according to the invention or used according to the invention is meant a proline specific endoprotease belonging to family S28 of the serine proteases (Handbook of Proteolytic Enzymes; Barrett A. J.; Rawlings N. D.; Woessner J. F., Eds.; Academic Press, London, UK, 1998, 369 415) or, more preferably, the polypeptide as mentioned in claims 1-5, 11 and 13 of WO 02/45524. Therefore this proline specific endo protease is a polypeptide which has proline specific endoproteolytic activity, selected from the group consisting of:

(a) a polypeptide which has an amino acid sequence which has at least 40% amino acid sequence identity with amino acids 1 to 526 of SEQ ID NO:2 or a fragment thereof;

(b) a polypeptide which is encoded by a polynucleotide which hybridizes under low stringency conditions with (i) the nucleic acid sequence of SEQ ID NO:1 or a fragment thereof which is at least 80% or 90% identical over 60, preferably over 100 nucleotides, more preferably at least 90% identical over 200 nucleotides, or (ii) a nucleic acid sequence complementary to the nucleic acid sequence of SEQ ID NO:1. The SEQ ID NO:1 and SEQ ID NO:2 as shown in WO 02/45524. Preferably the polypeptide is in isolated form.

The preferred polypeptide used according to the present invention has an amino acid sequence which has at least 50%, preferably at least 60%, preferably at least 65%, preferably at least 70%, more preferably at least 80%, even more preferably at least 90%, most preferably at least 95%, and even most preferably at least about 97% identity with amino acids 1 to 526 of SEQ ID NO: 2 or comprising the amino acid sequence of SEQ ID NO:2.

Preferably the polypeptide is encoded by a polynucleotide that hybridizes under low stringency conditions, more preferably medium stringency conditions, and most preferably high stringency conditions, with (i) the nucleic acid sequence of SEQ ID NO:1 or a fragment thereof, or (ii) a nucleic acid sequence complementary to the nucleic acid sequence of SEQ ID NO: 1.

The term "capable of hybridizing" means that the target polynucleotide of the invention can hybridize to the nucleic acid used as a probe (for example, the nucleotide sequence set forth in SEQ. ID NO: 1, or a fragment thereof, or the complement of SEQ ID NO: 1) at a level significantly above background. The invention also includes the polynucleotides that encode the proline specific endoprotease of the invention, as well as nucleotide sequences which are complementary thereto. The nucleotide sequence may be RNA or DNA, including genomic DNA, synthetic DNA or cDNA. Preferably, the nucleotide sequence is DNA and most preferably, a genomic DNA sequence. Typically, a polynucleotide of the invention comprises a contiguous sequence of nucleotides which is capable of hybridizing under selective conditions to the coding sequence or the complement of the coding sequence of SEQ ID NO: 1. Such nucleotides can be synthesized according to methods well known in the art.

A polynucleotide of the invention can hybridize to the coding sequence or the complement of the coding sequence of SEQ ID NO:1 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1 is typically at least 10 fold, preferably at least 20 fold, more preferably at least 50 fold, and even more preferably at least 100 fold, as intense as interactions between other polynucleotides and the coding sequence of SEQ ID NO: 1. The intensity of interaction may be measured, for example, by radiolabelling the probe, for example with 32P. Selective hybridization may typically be achieved using conditions of low stringency (0.3M sodium chloride and 0.03M sodium citrate at about 40° C.), medium stringency (for example, 0.3M sodium chloride and 0.03M sodium citrate at about 50° C.) or high stringency (for example, 0.3M sodium chloride and 0.03M sodium citrate at about 60° C.).

The UWGCG Package provides the BESTFIT program which may be used to calculate identity (for example used on its default settings).

The PILEUP and BLAST N algorithms can also be used to calculate sequence identity or to line up sequences (such as identifying equivalent or corresponding sequences, for example on their default settings).

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold. These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix alignments (B) of 50, expectation (E) of 10, M=5, N=4, and a comparison of both strands.

The BLAST algorithm performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The strains of the genus *Aspergillus* have a food grade status and enzymes derived from these micro-organisms are known to be from an unsuspect food grade source. According to another preferred embodiment, the enzyme is secreted by its producing cell rather than a non-secreted, socalled cytosolic enzyme. In this way enzymes can be recovered from the cell broth in an essentially pure state without expensive purification steps. Preferably the enzyme has a high affinity towards its substrate under the prevailing pH and temperature conditions.

MATERIALS AND METHODS

Figure 1:
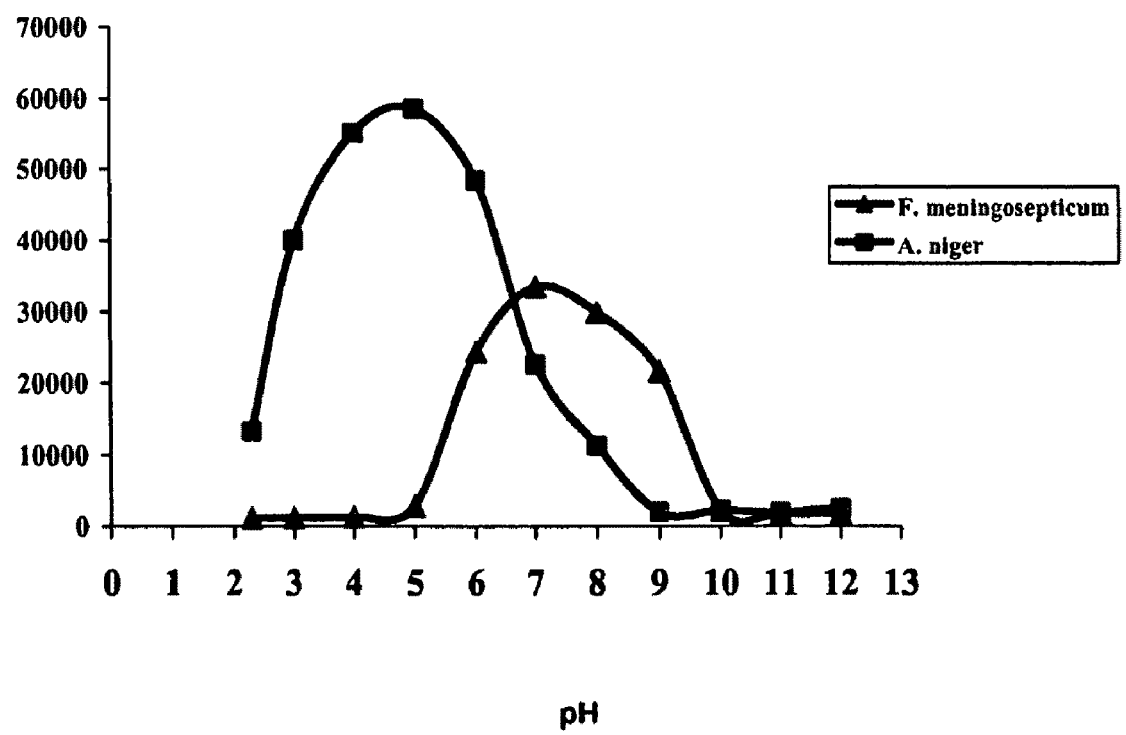
FIG. 1: Activity profiles of the proline-specific oligopeptidase of *F. meningosepticum* and the proline-specific endoprotease from *A. niger* measured on the fluorescent substrate Z-Gly-Pro-AMC under various pH conditions. Fluorescence was measured after 30 minutes at 37° C.

Edible sodium and potassium caseinate spray (88%) was obtained from DMV International, The Netherlands. GMP was obtained from Arla, Denmark (Lacprodan CGMP-10, lot # P340205). Synthetic chromogenic peptides were obtained from either Pepscan Systems B.V. The Netherlands or from Bachem, Switzerland. Flavourzyme 1000 L Batch HPN00218 was obtained from Novozymes (Denmark), Sumizyme FP from Shin Nihon (Japan) and Corolase LAP Ch.: 4123 from AB Enzymes. (UK).

Proline-Specific Endoprotease from *A. niger*.

Overproduction of the proline specific endoprotease from *Aspergillus niger* was accomplished as described in WO 02/45524. The activity of the enzyme was tested on the synthetic peptide Z-Gly-Pro-pNA at 37 degrees C. in a citrate/disodium phosphate buffer pH 4.6. The reaction product was monitored spectrophotometrically at 405 nM. A unit is defined as the quantity of enzyme that liberates 1 μmol of p-nitroanilide per minute under these test conditions and at a substrate concentration of 0.37 mM Z-Gly-Pro-pNA.

Chromatographic Purification of the *A. niger* Derived Endoprotease

The culture broth obtained from an overproducting *A. niger* strain was used for chromotograhpic purification of the protease to remove any contaminating endo- and exoproteolytic activities. To that end the fermentation broth was first centrifuged to remove the bulk of the fungal mass and the supernatant was then passed through a number of filters with decreasing pore sizes to remove all cell fragments. Finally, the ultrafiltrate obtained was diluted ten times in 20 millimol/liter sodium acetate pH 5.1 and applied on a Q-Sepharose FF column. Proteins were eluted in a gradient from 0 to 0.4 moles/liter NaCl in 20 millimol/liter sodium acetate pH 5.1. Peak fractions displaying activity towards the cleavage of Z-Gly-Pro-pNA were collected and pooled, according to the protocol described in World Journal of Microbiology & Biotechnology 11, 209-212 (1995), but under slightly modified assay conditions. Taking the acid pH optimum of the *A. niger* derived proline-specific endoprotease into account, the enzyme assay was carried out at pH 4.6 in a citrate/diphosphate buffer at 37° C. Pooling of the active fractions followed by concentration finally yielded a preparation which showed only a single band on SDS-PAGE and one peak on HP-SEC. Further analysis by hydrophobic interaction chromatography confirmed the purity of the enzyme preparation obtained.

Kjeldahl Nitrogen

Total Kjeldahl Nitrogen was measured by Flow Injection Analysis. Using a Tecator FIASTAR 5000 Flow Injection System equipped with a TKN Method Cassette 5000-040, a Pentium 4 computer with SOFIA software and a Tecator 5027 Autosampler the ammonia released from protein containing solutions was quantitated at 590 nm. A sample amount corresponding with the dynamic range of the method (0.5-20 mg N/l) is placed in the digestion tube together with 95-97% sulphuric acid and a Kjeltab subjected to a digestion program of 30 minutes at 200 degrees C. followed by 90 minutes at 360 degrees C. After injection in the FIASTAR 5000 system the nitrogen peak is measured from which the amount of protein measured can be inferred.

Amino Acid Analysis

A precisely weighed sample of the proteinaceous material was dissolved in dilute add and precipitates were removed by centrifugation in an Eppendorf centrifuge. Amino acid analysis was carried out on the clear supernatant according to the PicoTag method as specified in the operators manual of the Amino Acid Analysis System of Waters (Milford Mass., USA). To that end a suitable sample was obtained from the liquid, then dried and subjected to vapour phase acid hydrolysis and derivatised using phenylisothiocyanate. The various derivatised amino acids present were quantitated using HPLC methods and added up to calculate the total level of free amino acids, including derivatised Ile, in the weighed sample. The amino acids Cys and Trp are not included in the data obtained in this analysis.

LC/MSIMS Analysis

HPLC using an ion trap mass spectrometer (Thermoquest®, Breda, the Netherlands) coupled to a P4000 pump (Thermoquest®, Breda, the Netherlands) was used in quantification of the peptides of interest, among these the tripeptides IPP, LPP and VPP, in the enzymatic protein hydrolysates produced by the inventive enzyme mixture. The peptides formed were separated using a Inertsil 3 ODS 3, 3 mm, 150*2.1 mm (Varian Belgium, Belgium) column in combination with a gradient of 0.1% formic acid in Milli Q water (Millipore, Bedford, Mass., USA; Solution A) and 0.1% formic acid in acetonitrile (Solution B) for elution. The gradient started at 100% of Solution A, kept here for 5 minutes, increasing linear to 5% B in 10 minutes, followed by linear increasing to 45% of solution B in 30 minutes and immediately going to the beginning conditions, and kept here 15 minutes for stabilization. The injection volume used was 50 microliters, the flow rate was 200 microliter per minute and the column temperature was maintained at 55° C. The protein concentration of the injected sample was approx. 50 micrograms/milliliter.

Detailed information on the individual peptides was obtained by using dedicated MS/MS for the peptides of interest, using optimal collision energy of about 30%. Quantification is performed in LC/MS/MS mode using electrospray positive ionization mode with a $C_{13}+N_{15}$ labelled IPP standard, using a calibration line also with labelled internal standard to correct for matrix effect. Identification is performed by retention time, precursor ion and de ratio of characteristic fragmentions.

The tripeptide LPP (M=325.2) was used to tune for optimal sensitivity in MS mode and for optimal fragmentation in MS/MS mode, performing constant infusion of 5 mg/ml, resulting in a protonated molecule in MS mode, and an optimal collision energy of about 30% in MS/MS mode, generating a B- and Y-ion series.

Prior to LC/MS/MS the enzymatic protein hydrolysates were centrifuged at ambient temperature and 13000 rpm for 10 minutes, filtered through a 0.22 µm filter and the supernatant was diluted 1:100 with MilliQ water.

The Degree of Hydrolysis (DH) as obtained during incubation with the various protolytic mixtures was monitored using a rapid OPA test (JFS, Vol 66, NO 5, 2001).

Example 1

The Enzyme as Obtained from *A. niger* Represents a New Class of Proline Specific Enzymes From the entire coding sequence of the *A. niger* derived proline specific endoprotease as provided in WO 02/45524 a protein sequence of 526 amino acids can be determined. The novelty of the enzyme was confirmed by BLAST searches of databases such as SwissProt, PIR and trEMBL. To our surprise, no clear homology could be detected between the *A. niger* enzyme and the known prolyl oligopeptidases. Closer inspection of the amino acid sequence, however, revealed low but significant homology to Pro-X carboxypeptidases (EC3.4.16.2), dipeptidyl aminopeptidases I (EC3.4.14.2), and thymus specific serine protease. All of these enzymes have been assigned to family S28 of serine peptidases (Handbook of Proteolytic Enzymes; Barrett A. J.; Rawlings N. D.; Woessner J. F., Eds.; Academic Press, London, UK, 1998, 369-415). Also the GxSYxG (SEQ ID NO: 12) configuration around the active site serine is conserved between these enzymes and the *A. niger* derived endoprotease. Additionally, members of family S28 have an acidic pH optimum, have specificity for cleaving at the carboxy-terminal side of proline residues and are synthesized with a signal sequence and propeptide just like the *A. niger* derived proline specific endoprotease. Also the size of the *A. niger* enzyme is similar to those the members of family S28. Therefore, the *A. niger* proline specific endoprotease appears to be a member of family S28 of serine proteases rather than the S9 family into which most cytosolic prolyl oligopeptidases including the enzyme obtained from *Flavobacterium meningosepticum* have been grouped. On the basis of these structural and physiological features we have concluded that the *A. niger* enzyme belongs to the S28 rather than the S9 family of serine proteases. An additional feature that discriminates the *A. niger* derived enzyme from the prolyl oligopeptidases belonging to the S9 family is the fact that, unlike the cytosolic prolyl endoproteases belonging to the latter family, the newly identified *A. niger* enzyme is secreted into the growth medium. This is the first report on the isolation and characterization of a member of family S28 from a lower eukaryote.

Example 2

The pH Activity Spectra of the *A. niger* Proline Specific Endoprotease and the Proline Specific Oligopeptidase from *F. meningosepticum*

To demonstrate the difference in pH optima that exist between the *Aspergillus* derived proline specific endoprotease and the proline specific oligopeptidase from *Flavobacterium meningosepticum*, we measured their activities under various pH conditions. The *Aspergillus* derived endoprotease was obtained as described in the Materials & Methods section. The *Flavobacterium* derived oligopeptidase was purchased from ICN Biomedicals (35 units/mg; cat no. 32082; Ohio, US).

To establish the pH activity spectra of the two enzymes, buffers with different pH values were prepared. Buffers ranging from pH 2.0 to 7.0 were prepared using 0.1 mol/l citrate, buffers ranging from pH 6.0 to 9.0 were prepared using 0.1 mol/l tris and buffers ranging from pH 8.0 to 12.0 were made using 0.2 mol/l glycine. The required pH values were adjusted using either HCl or NaOH. The chromogenic synthetic peptide Z-Gly-Pro-AMC (Bachem, Switzerland) was used as the substrate for both enzymes. In each well (Costar no. 3631 plates) 85 uL of buffer, 10 uL of enzyme solution and 5 uL of the substrate (4 mM Z-Gly-Pro-AMC in 60% methanol) was introduced. Final concentration of the *A. niger* enzyme was 32 ug/ml (3.2 milli units/ml), final concentration of the *F. meningosepticum* enzyme was 0.21 ug/ml (7.4 milli units/ml). After mixing the reaction was allowed to proceed for 30 minutes at 37.0° C. after which the fluorescence was measured in a CytoFluor multi-well plate reader of PerSeptive Biosciences. The relative data as obtained are shown in FIG. 1. Also the temperature optimum of the prolyl endoprotease was established. To that end the purified enzyme preparation was incubated in 0.1 mol/l Na-acetate containing 0.02 mol/l $CaCl_2$ at pH 5.0 for 2 hours at different temperatures using Caseine Resorufine (Roche version 3) as the substrate and enzyme activity was quantified by measuring at 574 nm. According to the results obtained the proline specific endoprotease from *A. niger* has a temperature optimum around 50 degrees C.

Example 3

The Specificity of the *A. niger* Derived Proline Specific Endoprotease

Figure 2:
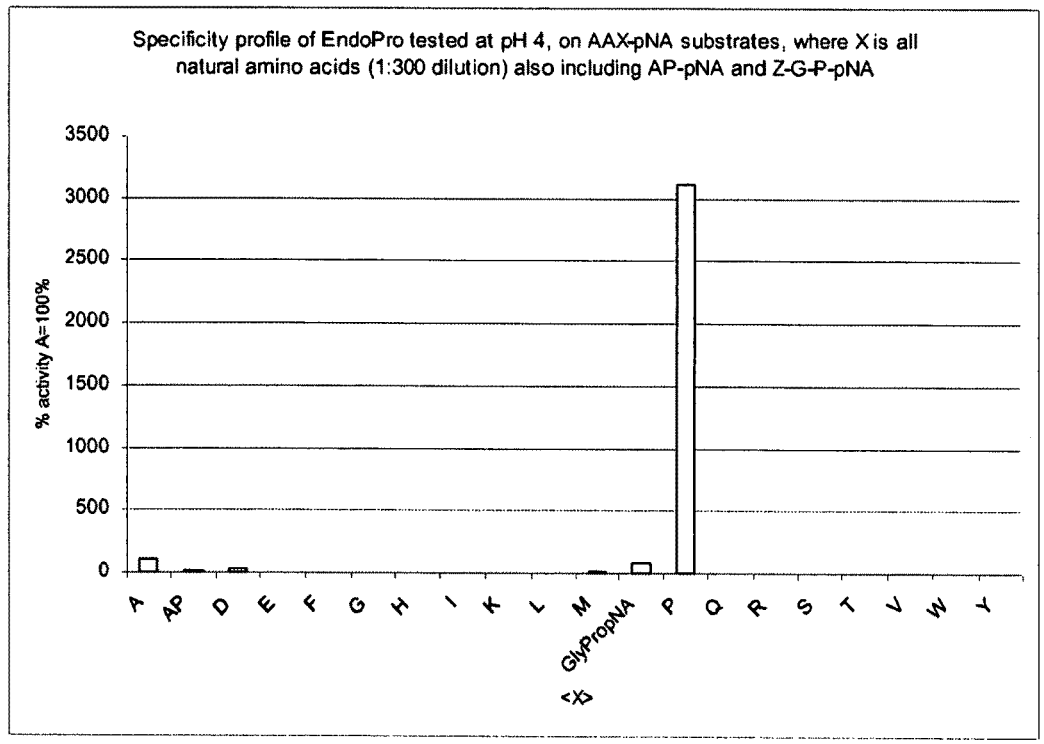
FIG. 2: Specificity profile of the *A. niger* derived prolyl endoprotease

Crude as well as chromatographically purified enzyme samples as obtained from an *A. niger* strain containing multiple copies of the expression cassette (cf WO 02/45524) were tested against a collection of chromogenic peptide substrates to establish the specificity of the encoded endoprotease. The endoproteolytic activity of the enzyme was tested on an AAXpNA substrate. The "pNA" (p-Nitroanilide) substrates cause color changes if the X-pNA peptide bond is cleaved; "X" represents different natural amino acid residues. Stock solutions of AAX-pNA substrates (150 mmol/l) were diluted 100× in 0.1M acetate buffer pH 4.0 containing 20 $CaCl_2$. The 10 minutes kinetic measurements at 40 degrees C. in a TECAN Genios MTP Reader (Salzburg, Vienna) at 405 nm recorded the increases in optical density that via data processing in Excel yielded the picture shown in FIG. 2. From the result it is clear that the *A. niger* derived endoprotease is highly specific for prolyl peptide bonds with a side activity towards alanyl bonds. Crude and chromatographically purified preparations showed similar activity profiles.

The contamination of the *A. niger* derived endoprotease with aminopeptidases, carboxypeptidases or non-proline specific endoproteases could be shown to be insignificant (see Example 5)

Example 4

The *A. niger* Derived Proline Specific Endoprotease can Hydrolyse Large Proteins as well as Small Peptides and is thus a True Endoprotease Owing to a specific structural feature, prolyl oligopeptidases belonging to the S9 family cannot digest peptides larger than 30 amino acids. This limitation is an obvious disadvantage for an enzyme, which is meant to hydrolyse as quickly and as efficiently as possible different proteins. To see if the *A. niger* derived proline specific endoprotease exhibits the same limitations with respect to the size of the substrate molecule, we have incubated the chromatographically purified prolyl endopeptidase from *A. niger* with a small synthetic peptide and with the large ovalbumine molecule and have analysed the hydrolysis products formed by SDS-PAGE.

The synthetic peptide used was a 27-mer of the sequence NH2-FRASDNDRVIDPGKVETLTIRRLHIPR-COOH (SEQ ID NO: 6) and was a gift of the Pepscan company (Lelystad, The Netherlands). As shown by its amino acid sequence, this peptide contains 2 proline residues, one in the middle and one near the carboxy terminal end of the peptide.

The intact ovalbumine molecule (Pierce Imject, vials containing 20 mg freeze dried material) consists of 385 amino acids with a molecular weight of 42 750 Da. This molecule contains 14 proline residues, one of which is located at the ultimate C-terminal end of the molecule and cannot be cleaved by a proline specific endoprotease. Ovalbumin and the oligopeptide were separately incubated at 50° C. with the purified *A. niger* derived proline specific endoprotease. At several time intervals samples were taken which were then analysed using SDS-PAGE.

A chromatographically purified *A. niger* derived proline specific endoprotease with an activity of 4.5 units/ml was diluted 100-fold with 0.1 M acetate buffer pH 4 containing 20 mM $CaCl_2$. The ovalbumine was dissolved in acetate buffer pH 4 to a concentration of 1 mg/ml (22 µM). The 27-mer was dissolved in the same buffer to reach a concentration of 0.48 mg/ml (152 µM). The molarity of the ovalbumine and the 27-mer solution was chosen in such a way that both solutions contained the same molarity in cleavable proline residues. Ovalbumine contains 13 potential proline cleavage sites, whereas the 27-mer peptide has only two. Of both substrate solutions 0.5 ml was incubated with 10 µl (0.45 milliU) of the enzyme solution in an Eppendorf thermomixer at 50° C. At several time intervals 10 µl samples were withdrawn from the incubation mixture and kept at 20° C. until SDS-PAGE. All materials used for SDS-PAGE and staining were purchased from Invitrogen. Samples were prepared using SDS buffer according to manufacturers instructions and separated on 12% Bis-Tris gels using MES-SDS buffer system according to manufacturers instructions. Staining was performed using Simply Blue Safe Stain (Collodial Coomassie G250).

Figure 3:
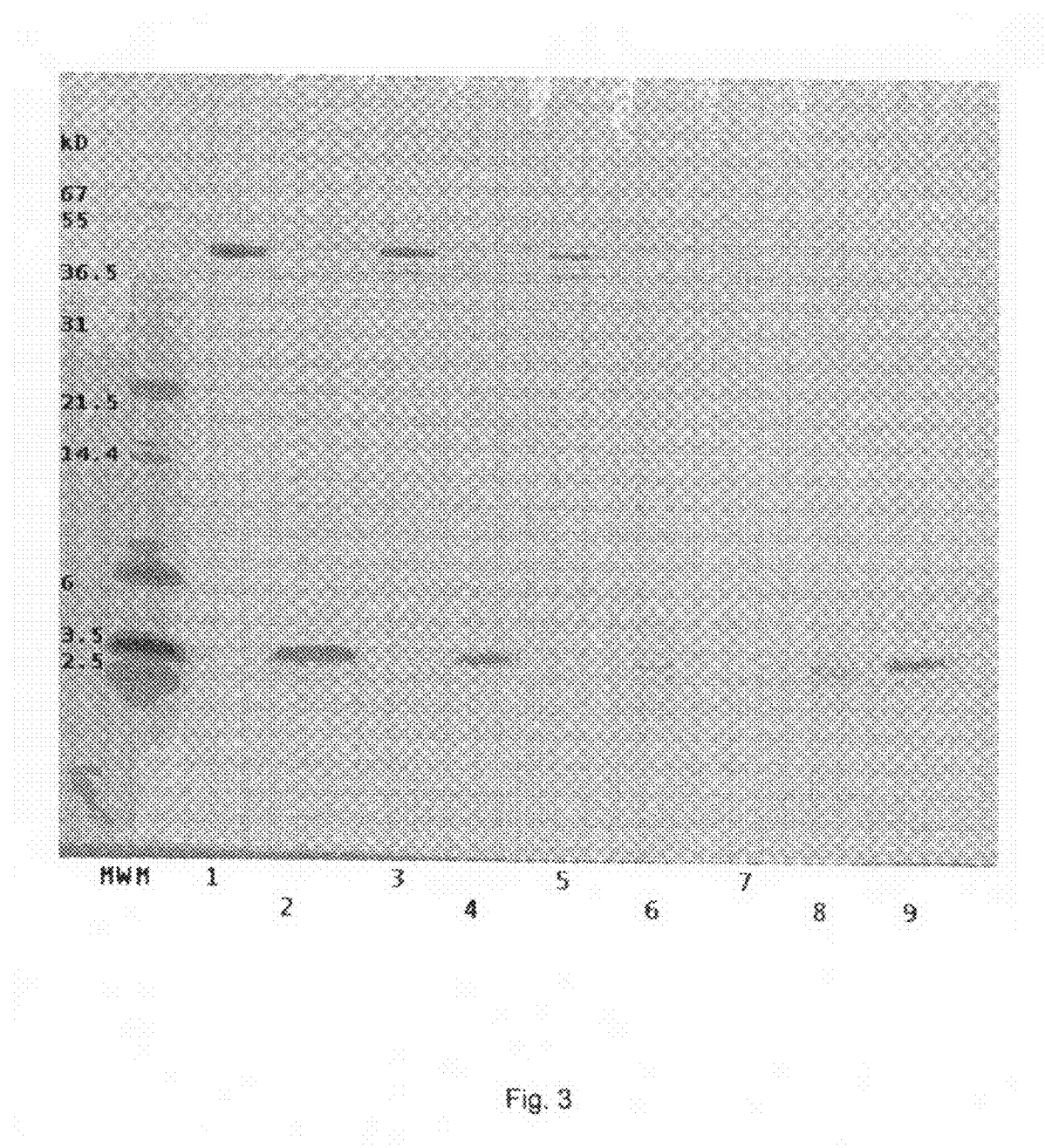
FIG. 3: SDS-PAGE of intact ovalbumine and a synthetic 27-mer peptide after incubation with chromatographically purified *A. niger* derived proline specific endoprotease.

As can be seen in FIG. 3 ovalbumine is cleaved by the *Aspergillus* derived enzyme into a discrete band of about 35 to 36 kD in the first 4.75 hours of incubation (lane 3). Prolonged incubation periods result in further breakdown to smaller products of various molecular weights (lane 7).

The 27-mer peptide is also broken down, as judged by the more faint bands in lanes 4, 6 and 8 as compared to lane 2. The very small molecular weight shift of the product (compare lanes 9 and 8) is most likely due to cleaving of the arginine residue at the carboxylic end of the peptide. The difference is about 200 D (measured using AlphaImager 3.3d software on an AlphaImager 2000 system) and arginine has a MW of 174. This small molecular weight shift is probably the first step in the breakdown of the peptide.

The further decay of the product can only be seen by the decrease in intensity of the band on the SDS gel. The products of further decay are not visible, as in gel staining of components with a MW of about 1000 is not possible with Coomassie Brilliant Blue. From this experiment it can be concluded that, unlike the known prolyl oligopeptidases belonging to the S9 family, the *A. niger* derived proline specific endoprotease has no specific preference for cleaving small sized peptides over much larger proteins. As such the *A. niger* derived enzyme represents a true endoprotease and a preferred enzyme to hydrolyse different types of proteins.

Example 5

The Quantitation of Desirable and Contaminating Enzyme Activities in the Production of Blood Pressure Lowering Peptides According to the present invention relatively pure IPP can be obtained in a simple one-step process by recovering IPP from GMP. The IPP containing fraction can be obtained from GMP by a variety of different enzyme preparations. For example, by incubating GMP with either a pure proline specific endoprotease, or a pure proline specific endoprotease plus a pure aminopeptidase, or a pure proline specific oligopeptidase in combination with a trace of another pure endopeptidase such as a subtilisin or a metalloprotease (to cleave GMP into smaller fragments forming improved substrates for the oligopeptidase), or a pure aminopeptidase in combination with a proline specific tripeptidyl aminopeptidase (as present in the commercial "Umamizyme" preparation from Amano, Japan), or complex enzyme preparations containing different kinds of proteolytic activities. In this Example three commercial enzyme preparations were tested for their various proteolytic activities i.e.: Flavourzyme 1000 L Batch HPN00218 (Novozymes), Sumizyme FP (Shin Nihon, Japan) and Corolase LAP Ch.: 4123 (AB Enzymes, UK). Both Flavourzyme and Sumizyme FP are known to be complex enzyme preparations that contain several aminopeptidolytic enzyme activities besides non-specified endoproteolytic and carboxypeptidolytic activities. Corolase LAP represents a relatively pure, cloned and overexpressed leucine aminopeptidase activity from *Aspergillus*.

Essentially pure meaning that the activity of contaminating endoproteases as well as contaminating carboxypeptidases or aminopeptidases under the incubation conditions used are minimal or preferably absent. The following testing procedure was devised to quantitate such contaminating endo-, amino- and carboxypeptidases activities.

The basis for the testing procedure is formed by a collection of various selective chromogenic peptides. Because only proline specific oligo- and endoproteases can release pNA from peptide Z-AAAP-pNA (SEQ ID NO: 7), this particular peptide was used to quantitate the desired proline specific endoproteolytic activity. Because many endoproteases can release pNA from peptides Z-AAA -pNA (SEQ ID NO: 8) and Z-AAAR-pNA (SEQ ID NO: 9), these two peptides were used to quantitate contaminating, non-proline specific endoproteolytic activity. Because the conversion of peptides QNIPP (SEQ ID NO: 10) and VVVPP (SEQ ID NO: 11) as present in the beta-caseine molecule into IPP and VPP respectively require aminopeptidases that can efficiently remove Gln and Val residues, peptides Q-pNA and V-pNA were used to quantitate desired aminopeptidase activities. Because many carboxypeptidases can release Phe and Arg residues from peptides, peptides containing these residues were selected to quantitate contaminating carboxypeptidase activities. However, no suitable chromogenic groups are available for measuring carboxypeptidase activities so that an alternative method using the synthetic peptides Z-AF and Z-AR had to be developed. This alternative method is provided underneath. In all the synthetic peptides used "Z" represents benzyloxycarbonyl and "pNA" the chromophore para-nitroanilide. All chromogenic peptides were obtained from Pepscan (Lelystad, The Netherlands). Peptides Z-AF and Z-AR were purchased from Bachem (Switserland). All incubations were carried out at 40° C. Diluted enzyme preparations were recalculated to the concentration of the commercial product.

Measuring Amino Peptidase Activities

Stock solutions of 150 mmol/l of V-pNA and Q-pNA in 100% DMSO were diluted 80 times in 0.1 M BisTris buffer pH 6 to make a 3.75 mmol/l V-pNA+Q-pNA-substrate solution containing V-pNA and Q-pNA in a 1:1 ratio. A 200 µl aliquot of this aminopeptidase substrate solution was pipetted into separate wells of a microtiterplate (MTP) The MTP is pre-incubated at 40° C. in a Tecan Genios MTP (Salzburg, Vienna) running under Magellan4 software. The reaction was started by adding 50 µl of the appropriate enzyme solution so that the incubations took place at a substrate concentration of 3 mM. Typically a 1:50 dilution of the liquid enzyme samples Flavourzyme, Corolase LAP and proline-specific endo-protease was used. Of the dry Sumizyme FP product a 1% solution was used.

The yellow color as measured at 405 nm by the Tecan Genios MTP developing as the result of cleavage of the amino acid-pNA bond was followed for at least 20 kinetic cycles (about 10 minutes). The software generated the data obtained as $OD_{405}$/min.

Measuring Proline Specific Endoprotease Activity.

This measurement was carried out essentially the same as the aminopeptidase assay but in this case Z-AAAP-pNA (SEQ ID NO: 7) was used as the only substrate in a final concentration of 3 mmol/l. This substrate was solubilized by heating a suspension in pH 6 buffer to 50-55° C. resulting in a clear solution at room temperature. Measurements were carried out at 40° C.

Typically a 1:50 dilution of the liquid enzyme samples Flavourzyme and Corolase LAP were used. Sumizyme FP was used in a 1% solution. The proline specific endo-protease was typically used in a 1:5000 dilution.

The software generated the data as $OD_{405}$/min.

Measuring Contaminating Non-Proline Specific Endoprotease Activities.

Also this measurement was carried out essentially the same as described for the aminopeptidase assay but in this test Z-AAAF-pNA (SEQ ID NO: 8) and Z-AAAR-pNA (SEQ ID NO: 9) in a 1:1 ratio and in a final concentration of 3 mmol/l were used as the substrate. The substrate Z-AAAF-pNA (SEQ ID NO: 8) turned out to be poorly soluble under the pH 6.0 test conditions used but a test incubation with subtilisin resulted in a rapid solubilisation of the substrate concomitantly with the pNA release. Measurements were carried out at 40° C. However, to compensate for this poor solubility the MTP reader was programmed to shake in between the kinetic cycles.

Again the software generated the data as $OD_{405}$/min.

Measuring Contaminating Carboxypeptidase Activities

Because no sensitive chromogenic peptides are available to measure carboxypeptidase activities, a method was used based on a Boehringer protocol for quantitating Carboxypeptidase C.

Two 150 mmol/l stock solutions in ethanol of Z-A-F and Z-A-R were diluted 80 times in 0.1 mol/l BisTris buffer pH 6 to make a 3.75 mmol/l Z-A-F+Z-A-R substrate solution containing Z-A-F and Z-A-R in a 1:1 ratio. Then 200 µl of the substrate solution was pipetted into an eppendorf vial and pre-incubated at 40° C. The reaction was started by adding 50 µl of an appropriate enzyme dilution. Typically a 1:50 dilution is used of Flavourzyme and Corolase LAP and the proline specific endoprotease. A 1% solution was used for Sumizym FP. After 5 minutes the reaction was stopped by adding 250 µl of ninhydrine reagent. Ninhydrine reagent was made of 400 mg ninhydrine (Merck) and 60 mg hydrindantin dissolved 15 ml DMSO, to which 5 ml of 4.0 mol/l lithium acetate buffer pH 5.2 was added. The 4.0 mol/l lithium acetate buffer was made by dissolving LiOH (Sigma) after which the pH of the solution was adjusted to pH 5.2 using glacial acetic acid (Merck).

After stopping the reaction, each sample was heated for 15 minutes at 95° C. to facilitate the color formation and subsequently diluted 10 times with pure ethanol. The color formed was measured at 578 nm in an Uvikon spectrophotometer. Blanks were made in the same manner as the activity samples, but ninhydrin reagent and enzyme addition were reversed. To quantitate the amount of free amino acids generated by the carboxypeptidase activity, the amino acid L-phenylalanine was used to create a calibration curve. Solutions in buffer pH 6 containing 0.1875, 0.375, 0.75, 1.5 and 3.0 mmol/l of L-phenylalanine (Sigma) were treated in the same manner as the samples, i.e. 250 µl in a vial. From the OD578 values obtained, a curve was constructed in Excel. The concentrations of the free amino acids present in the samples containing the Z-A-F and Z-A-R substrates were calculated using this curve. From the values obtained the carboxy-peptidase activity was calculated in micromoles per minute per the amount of enzyme tested.

Calculation of Activity Ratios

To establish the suitability of various enzyme preparations for the process according to the invention, quotients of the relevant enzyme activities were calculated. In the MTP reader based assays, enzyme activities are characterised by pNA release over time i.e. as $\Delta OD_{405}$/min. Quotients of enzyme activities obtained by the MTP reader were calculated by simply dividing the ΔOD/min values obtained for identical quantities of enzyme.

However in case of the carboxy-peptidase assay, an OD is generated that cannot be compared directly to the ΔOD/min generated by the MTP-PNA based assays. Here the OD measured was first converted to µmol amino acid released per min (µmol/min). Then the ΔOD/min of pNA released was converted into µmol/min. To that end a calibration curve was generated in the MTP reader in which dilutions of pure pNA (Sigma) 0.25, 0.125, 0.0625, 0.0312 and 0.015 mmol/l and 250 µl per well were measured. From the data obtained a calibration curve was constructed in Excel. From this calibration curve the ΔOD/min was converted into µmol/min so that the pNA based measurements could be compared with the ninhydrin based measurements.

On the basis of the data generated in the above-mentioned tests, the various enzyme preparations used were characterised. The data on the proline specific oligo- or endoproteolytic activities present in each enzyme preparation as provided are shown in Table 1 in the column "Prol Spec Activity". The data on the desired aminopeptidase activities (AP/Prol Spec Act) and the contaminating carboxypeptidase (CPD/Prol Spec Act) and endoproteolytic activities (Endo/Prol Spec Act) are shown relative to the proline specific activities present. The desired aminopeptidase activity relative to the contaminating carboxypeptidase activity as present in each preparation is shown as (AP/CPD).

Evident is that none of the commercial enzyme preparations tested contains any significant proline specific oligo- or endoproteolytic activity. Furthermore all commercial enzyme preparations tested contain carboxypeptidase and endoproteolytic activities. Enzyme combination C1 consists of a mixture of 4 units proline specific endoprotease plus 130 microliter of the commercial Corolase LAP to be applied per gram of proteinaceous substrate present that generates high yields of ACE inhibiting IPP, VPP and LPP peptides stands out because of its very low levels of contaminating carboxypeptidase and endoproteolytic activities.

TABLE 1

|  | Prol Spec Activity* | CPD/ Prol spec act | AP/ Prol spec act | Endo/ Prol spec act | AP/ CPD |
|---|---|---|---|---|---|
| Sumizyme | 0.004 | 21.7 | 1.2 | 1.7 | 0.06 |
| Flavourzyme | 0.0007 | 253.5 | 25.6 | 35.5 | 0.10 |
| Corolase LAP | 0.0 |  |  |  | 0.74 |
| Prol spec A. niger | 100 | 0.005 | 0.00001 | 0.000004 | 0.00 |
| C1 | 75 | 0.001 | 0.00031 | 0.000391 | 0.25 |

*Sumizyme was measured in a 1% solution, Flavourzyme and Corolase as a 1:50 dilution. Prol specific activity as obtained from A. niger was measured as 1:5000 dilution and C1 as a 1:3773 dilution. Data were then calculated to the activity present in the product as provided.

On the basis of their high content of amino- and carboxypeptidase activities, incubations of GMP with the complex enzyme mixtures Sumizyme FP and Flavourzyme can be expected to generate high levels of free amino acids. These free amino acids can be expected to impart brothy off tastes as the result of increased Maillard reactions. Furthermore the presence of non-proline or non-alanine specific endoproteolytic activities in these enzyme preparations will lead to the solubilisation of additional and perhaps bioactive peptides in the final product hereby blurring the pure blood pressure lowering effect of IPP. To minimise all these undesirable side reactions, the combination of an essentially pure proline specific protease with an essentially pure aminopeptidase is preferred. Even more preferred is the use of only an essentially pure proline specific endoprotease.

Example 6

Isolating GMP and IPP from Caseinate

Commercially available GMP is obtained from cheese whey. In this process milk is incubated with chymosin to release the water-soluble GMP part from kappa-casein. As a result the caseinate precipitates to form the curd whereby the GMP part ends up in the cheese whey from which it can be isolated by a number of different processes. In this Example we describe an alternative route for the isolation of GMP i.e. an isolation from commercially available caseinate. Advantage of this route is that after the selective removal of the GMP, the remaining caseinate fraction can be used for alternative applications. According to the present process (skim) milk is acidified according to methods known in the art to selectively precipitate the casein fraction. The precipitated fraction incorporates all caseins, i.e. the alpha, beta, kappa (including the GMP part) and gamma-caseins. This casein curd formed is separated from the "sweet whey" fraction and washed to remove remaining whey components and the ions generated by the acidification process. After dewatering the casein curd is re-dissolved by neutralization, for example using KOH, to yield the relevant "caseinate".

A 10% (w/v) potassium-caseinate solution (approx. pH 6.4) was incubated at 31 degrees C. for 1 hour with calf chymosin to release the GMP part from kappa-casein. In this case 2.2 IMCU Maxiren (DSM Food Specialties, Delft, The Netherlands) was used per gram caseinate. The resulting solution was subjected to one or more filtration steps to separate the dissolved, low molecular weight GMP part from the large molecular weight fraction containing both the caseins and the chymosin. The GMP containing permeate was acidified to pH 4.5 and the A. niger derived proline specific endoprotease was added in a concentration of 4 units per gram of protein present. The temperature was increased to 55 degrees C. to maximize the activity of the enzyme and incubation was pursued for 3 hours. The resulting solution was then concentrated by evaporation and heated for 5 minutes to 95 degrees C. to inactivate the proline specific endoprotease. Finally the heated concentrate was ultrafiltered to remove precipitated proteins as much as possible and spray dried. According to LC/MS/MS analysis of the spray dried material the IPP concentration was quantitated to be 0.6 milligram of IPP per gram caseinate starting material.

Example 7

Liberating IPP from GMP in a Single Incubation Step

A series of incubations was carried out to demonstrate that the proline specific endoprotease from A. niger and Sumizyme FP are suitable to liberate the blood pressure lowering tri-peptide IPP from GMP. In this experiment a commercially available GMP preparation was used (Lacprodan CGMP-10, lot # P340205 from Ada, Denmark). According to its specifications the powder as obtained contains approx 85% protein with a GMP content of about 80% (of the protein present), i.e. 1 gram Lacprodan CGMP-10 powder contains approx. 0.85× 0.8=0.7 grams of pure GMP.

The GMP was dissolved in demineralised water (50 grams GMP in 450 ml). The pH of this solution is 6.7. Of this solution 135 ml were brought to pH 4 using 4N HCl and additional water was added to reach a volume of 150 ml and a GMP concentration of 10% solids. Of the pH 6.7 solution 45 ml were brought to pH 6 with 4 N HCl and 90 ml to pH 8 using 4N KOH. To both solutions extra water was added to also reach a concentration of 10% GMP solids. The pH 4.0 of the incubation with the proline specific endoprotease was chosen as pH 4 represents the optimum for this enzyme. Because Sumizyme FP consists of a mixture of various endoproteases, aminopeptidases and carboxypeptidases all with their own pH optima, this incubation was carried out under different pH conditions.

With these three solutions adjusted to various pH values, incubations with the various enzymes were carried out as shown in Table. The proline specific endoprotease was used in a concentration of 0.4 U/ml (~4.2 U/gr protein) and Sumizyme FP in a 1 mg/ml final concentration (~10.4 mg/gr protein). All incubations were done in 50 ml conical Greiner tubes in a water bath set at 40° C. for 6 hours under mild shaking. After the incubations the samples were kept frozen at −20° C. until LC/MS/MS analysis. The data as obtained in the latter analysis are shown in Table and were measured using IPP, VPP and LPP reference solutions.

TABLE 2

Incubation scheme of GMP solutions with MaxiPro and Sumizyme FP

| Incubation nr | Mls of 10% GMP solution | Mls of 10 units/ml prol spec enzyme solution | Mls of 25 mg/ml Sumizyme FP solution | pH of incubation mixture |
|---|---|---|---|---|
| 1 | 48 | — |  | 6.7 |
| 2 | 48 | 2 |  | 4 |
| 3 | 48 | — | 2 | 4 |
| 4 | 48 | — | 2 | 6 |
| 5 | 48 | — | 2 | 8 |

TABLE 3

Yield of peptides upon enzym incubation of the various GMP solutions

| Incubation | IPP | | VPP | | LPP | |
|---|---|---|---|---|---|---|
| No | microgr/ml | microgr/gr | microgr/ml | microgr/gr | microgr/ml | microgr/gr |
| 1 | nd | nd | nd | nd | nd | nd |
| 2 | 1657 | 2367 | nd | | nd | |
| 3 | 41 | 59 | 3 | 4 | 6 | 9 |
| 4 | 389 | 556 | 36 | 51 | nd | |
| 5 | 570 | 814 | 44 | 63 | nd | |

Microgr/ml = microgram of the relevant tripeptide per ml of 10% GMP solution
Microgr/gr = microgram of the relevant tripeptide per gram of GMP protein
nd = not detectable From the results obtained it is clear that incubation with the pure proline specific endoprotease yields an IPP containing product devoid of the peptides VPP and LPP.

The quantity of IPP as released in this non-optimized incubation represents approx 50% of the IPP moiety present in GMP.

Most importantly the incubations with the complex Sumizyme FP enzyme also lead to the formation of IPP from GMP. According to our data most efficiently under pH 8 conditions. The fact that with Sumizyme FP the IPP yields are lower than in the incubation with the proline specific endoprotease merely reflects a situation of under-dosing of the Sumizyme FP enzyme in this experiment. Quite surprisingly Sumizyme FP did not only generate IPP but also VPP and LPP from the Lacprodan material. As the tripeptides VPP and LPP occur in the beta-casein amino acid sequence only, their presence clearly illustrates the fact that the GMP material as obtained is contaminated with beta-casein.

Example 8

To demonstrate the organoleptical benefits of an IPP containing hydrolysate obtained from GMP, a tasting experiment was conducted. In this experiment three different substrates, i.e. GMP, potassium caseinate and skim milk were incubated with the proline specific endoprotease from A. niger. Using this pure enzyme, only the IPP present in the kappa casein molecule can be excised (cf. WO 2006/005757). All three incubations contained the same protein concentration of 3.5% (w/w) of protein and contained the same quantity of enzyme, i.e, 4 units/gram protein. To prevent precipitation of the caseins, the pH of the solutions was adjusted to 6.2. Incubation was allowed to proceed for 3 hours and was then terminated by a short heat treatment.

In all three hydrolysates a significant precipitate was present. After centrifugation to remove these precipitates, the clear (IPP containing) supernatants were tasted by a trained panel consisting of 5 people. Panel members were trained with quinine sulphate solutions with the following concentrations: 15 mg/L quinine sulphate>Intensity bitter=1, 20 mg/L quinine sulphate>Intensity bitter=2, 30 mg/L quinine sulphate>Intensity bitter=3 and 50 mg/L quinine sulphate>Intensity bitter=4. The panel scored the bitterness of each hydrolysate on a scale of 0 (not bitter) to 4 (very bitter). A reference sample of 15 mg/L quinine sulphate was given to the panellists before the taste session and was assigned a bitter intensity value of 1. The casein hydrolysate was judged to be very bitter i.e. 4 with all members of the taste panel. The skim milk hydrolysate was also bitter scoring a 3 with all members of the panel. Upon tasting the GMP hydrolysate, the panel unanimously gave a score of 1. Taking into account that the GMP hydrolysate also can be expected to yield the highest concentration of IPP, the surprising benefits of the process according to the present invention are clearly demonstrated.

Example 9

Liberating IPP from GMP by Fermentation

The poor palatability of fermented milk products and the many processing difficulties encountered during the recovery of ACE inhibiting peptides from fermented broths have been described in U.S. Pat. No. 6,428,812. In this Example we demonstrate that the GMP molecule also is a suitable substrate for the production of IPP by fermentation.

Two Lactobacillus strains, Lactobacillus acidophilus LAFTI® L10 and Lactobacillus casei LAFTI® L26 (DSM Food Specialties, Australia) were used in this study. Both strains were grown in anaerobic jars under $CO_2+N_2$ atmosphere (AnaeroGen™, Oxoid) at 37° C. in MRS broth (Oxoid) for 24 h. The resulting precultures were then inoculated in fermentation broth "a" or fermentation broth "ay". Fermentation broth "a" contained: Tween 80 (1 ml/l), $K_2HPO_4$ (2 g/l), NaAc (3 g/l), $(NH_4)_3$Citrate (2 g/l), $MgSO_4.7H_2O$ (0.2 g/l), $MnSO_4.4H_2O$ (0.05 g/l), glucose (20 g/l), GMP (Lacprodan, Ada; 22 g/l). Fermentation broth "ay" also contained yeast extract (4.0 g/l). The newly inoculated fermentation broths "a" and "ay" were incubated for another 24 hours under the conditions outlined above. Thereafter, these fermentation broths were centrifuged and the supernatants were analysed by LC/MS for the presence of the tripeptides IPP, LPP and VPP. As illustrated in Table 4, only in the incubations with strain L10 the presence of IPP could be detected at a level of 0.3 mg/l. LPP and VPP were not present. The tasting of samples 1 and 5 did not reveal significant off-tastes.

TABLE 4

Liberating IPP from GMP by fermentation

| Tube | Fermentation broth | Strain | IPP production |
|---|---|---|---|
| 1 | a | L10 | yes |
| 2 | ay | L10 | yes |
| 3 | a | L26 | not detected |
| 4 | ay | L26 | not detected |
| 5 | a | without inoculum as control | not detected |

The invention claimed is:

1. A process to produce IPP from a protein source, at least 90% of the protein source being the glycomacropeptide fragment of kappa casein ("GMP"), which comprises hydrolysing the protein source to liberate at least 20% of the I-P-P- sequence into the peptide IPP and wherein a proteolytic enzyme is used which cleaves at the carboxy-terminus of proline residues present in the protein source and, optionally, an amino peptidase.

2. The process according to claim 1 wherein soluble peptides, including IPP, which are formed during hydrolysing the protein source, are separated and optionally dried.

3. The process according to claim 1 wherein the proteolytic enzyme which cleaves at the carboxy-terminus of proline is a proline specific endoprotease or proline specific oligopeptidase.

4. The process according to claim 3 wherein the proteolytic enzyme which cleaves at the carboxy-terminus of proline is a proline specific endoprotease.

5. The process according to claim 1 wherein the protein source comprises a mixture of proteins comprising at least 90% of protein which are free of -V-P-P-.

6. The process according to claim 5 wherein the protein source comprises a mixture of proteins comprising at least 95% of protein which are free of -V-P-P-.

7. The process according to claim 1 wherein at least 40% of -I-P-P- sequence present in GMP is converted into the peptide IPP.

8. The process according to claim 7 wherein at least 60% of -I-P-P- sequence present in GMP is converted into the peptide IPP.

9. The process according to claim 8 wherein at least 70% of -I-P-P- sequence present in GMP is converted into the peptide IPP.

* * * * *

SEQUENCE LISTING

<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Val Pro Pro
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Val Pro Pro
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ile Pro Pro
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Ile Pro Pro
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ser Thr Pro
1

<210> SEQ ID NO 6
<211> LENGTH: 27
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 6

Phe Arg Ala Ser Asp Asn Asp Arg Val Ile Asp Pro Gly Lys Val Glu
1               5                   10                  15

Thr Leu Thr Ile Arg Arg Leu His Ile Pro Arg
            20                  25

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Benzyloxycarbonyl-Ala
<220> FEATURE:
<221> NAME/KEY: MOD_RES
<222> LOCATION: (4)..(4)
<223> OTHER INFORMATION: Pro-para-nitroanilide

<400> SEQUENCE: 7

Ala Ala Ala Pro
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Benzyloxycarbonyl-Ala
<220> FEATURE:
<221> NAME/KEY: MOD_RES
<222> LOCATION: (4)..(4)
<223> OTHER INFORMATION: Phe-para-nitroanilide

<400> SEQUENCE: 8

Ala Ala Ala Phe
1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Benzyloxycarbonyl-Ala
<220> FEATURE:
<221> NAME/KEY: MOD_RES
<222> LOCATION: (4)..(4)
<223> OTHER INFORMATION: Arg-para-nitroanilide

<400> SEQUENCE: 9

Ala Ala Ala Arg
1

<210> SEQ ID NO 10
<211> LENGTH: 5
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Asn Ile Pro Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Val Val Pro Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 12

Gly Xaa Ser Tyr Xaa Gly
1               5
```